(12) United States Patent  
Horn

(10) Patent No.: US 9,400,253 B2  
(45) Date of Patent: Jul. 26, 2016

(54) IN-SITU MEASUREMENTS OF SPATIALLY RESOLVED SPECTROSCOPIC DATA WITHIN A REACTOR CHAMBER OF A REACTOR

(75) Inventor: Raimund Horn, Berlin (DE)

(73) Assignee: Technische Universitaet Hamburg-Harburg, Hamburg (DE)

(*) Notice: Subject to any disclaimer, the term of this patent is extended or adjusted under 35 U.S.C. 154(b) by 971 days.

(21) Appl. No.: 13/515,986

(22) PCT Filed: Dec. 15, 2009

(86) PCT No.: PCT/EP2009/008973  
§ 371 (c)(1),  
(2), (4) Date: Aug. 27, 2012

(87) PCT Pub. No.: WO2011/072701  
PCT Pub. Date: Jun. 23, 2011

(65) Prior Publication Data  
US 2012/0309101 A1 Dec. 6, 2012

(51) Int. Cl.  
*G01N 21/76* (2006.01)  
*G01N 21/85* (2006.01)  
(Continued)

(52) U.S. Cl.  
CPC ............ *G01N 21/8507* (2013.01); *G01N 21/31* (2013.01); *G01N 21/33* (2013.01);  
(Continued)

(58) Field of Classification Search  
CPC .................. G01N 27/44721; G01N 27/44782; G01N 2021/0346; G01N 21/4788; G01N 30/74; G01N 2021/6419; G01N 2021/6484; G01N 21/255; G01N 21/51; G01N 21/53; G01N 15/1459; G01N 27/44743; G01N 30/466  
See application file for complete search history.

(56) References Cited

U.S. PATENT DOCUMENTS 4,676,955 A 6/1987 Berty  
5,051,551 A 9/1991 Doyle  
(Continued)

FOREIGN PATENT DOCUMENTS

DE 30 28 013 A1 2/1982  
DE 198 43 553 A1 4/2000

OTHER PUBLICATIONS

Utzinger and Richards-Kortum, "Fiber Optic Probes in Optical Spectroscopy Clinical Applications", Electronic Spectroscopy Applications, 1999, pp. 512-528.*

(Continued)

*Primary Examiner* — Yelena G Gakh  
(74) *Attorney, Agent, or Firm* — RatnerPrestia

(57) ABSTRACT

A system for in-situ spectroscopic measurements in heterogeneous catalytic reactors includes a reactor having a reactor chamber, a device for collecting a sample, and a device for collecting spectroscopic information. The device for collecting the sample includes a sampling capillary having an orifice situated inside the reactor chamber. The device for collecting spectroscopic information includes at least one optical radiation guide for guiding optical radiation onto the sample for excitation and for collecting optical radiation emitted, absorbed, reflected or scattered by the sample. The at least one optical radiation guide may be inserted into the sampling capillary, such that a tip of the at least one optical radiation guide is proximate to the orifice. A method for analyzing a reactor state including the steps of providing a reactor; collecting spectroscopic information from a sample inside the reactor chamber; and analyzing the collected spectroscopic information is also provided.

14 Claims, 11 Drawing Sheets

(51) Int. Cl.

| | | |
|---|---|---|
| G01N 21/31 | (2006.01) | |
| G01N 21/33 | (2006.01) | |
| G01N 21/35 | (2014.01) | |
| G01N 21/64 | (2006.01) | |
| G01N 21/65 | (2006.01) | |
| G01N 21/3504 | (2014.01) | |
| G01N 21/3563 | (2014.01) | |
| G01N 21/3577 | (2014.01) | |

(52) U.S. Cl.
CPC ........... *G01N 21/35* (2013.01); *G01N 21/3504* (2013.01); *G01N 21/3563* (2013.01); *G01N 21/3577* (2013.01); *G01N 21/64* (2013.01); *G01N 21/65* (2013.01); *G01N 2021/8535* (2013.01)

(56) References Cited

U.S. PATENT DOCUMENTS

| | | | |
|---|---|---|---|
| 5,170,056 A | | 12/1992 | Berard et al. |
| 5,434,084 A | * | 7/1995 | Burgess, Jr. .......... G01N 21/643 356/41 |
| 6,723,804 B1 | | 4/2004 | Battiste |
| 2002/0126289 A1 | | 9/2002 | Marquardt et al. |
| 2007/0019190 A1 | | 1/2007 | Marrow et al. |
| 2007/0107618 A1 | | 5/2007 | Lacroix et al. |

OTHER PUBLICATIONS

Utzinger and Richards-Kortum, "Fiber Optic Probes for Biomedical Optical Spectroscopy", J. Biomed. Optics, Jan. 2003, v. 8, No. 1, pp. 121-147.*
Geske et al. in "Resolving kinetics and dynamics of a catalytic reaction inside a fixed bed reactor by combined kinetic and spectroscopic profiling", Catal. Sci. Technol., 2013, v. 3, pp. 169-175.*
Utzinger and Richards-Kortum, "Fiber optic probes for biomedical optical spectroscopy", J. Biomed. Optics, 2003, v. 8, No. 1, pp. 121-147.*
Horn et al., "Methane catalytic partial oxidation on autothermal Rh and Pt foam catalysts: Oxidation and reforming zones, transport effects, and approach to thermodynamic equilibrium," *Journal of Catalysis*, 2007, vol. 249, pp. 380-393.
Bosco et al., "Optically accessible channel reactor for the kinetic investigation of hydrocarbon reforming reactions," *Catalysis Today*, 2006, vol. 116, pp. 348-353.
Horn et al., "Spatial and temporal profiles in millisecond partial oxidation processes," *Catalysis Letters*, Sep. 2006, vol. 110, Nos. 3-4, pp. 169-178.
Horn et al., "Syngas by catalytic partial oxidation of methane on rhodium: Mechanistic conclusions from spatially resolved measurements and numerical simulations," *Journal of Catalysis*, 2006, vol. 242, pp. 92-102.
Urschey et al., "A low cost reactor for high-throughput activity screening of heterogeneous catalysts by mass spectrometry," *Solid State Science*, 2003, vol. 5, pp. 909-916.
International Search Report dated Nov. 23, 2010, from PCT International Application No. PCT/EP2009/008973.

* cited by examiner (a)

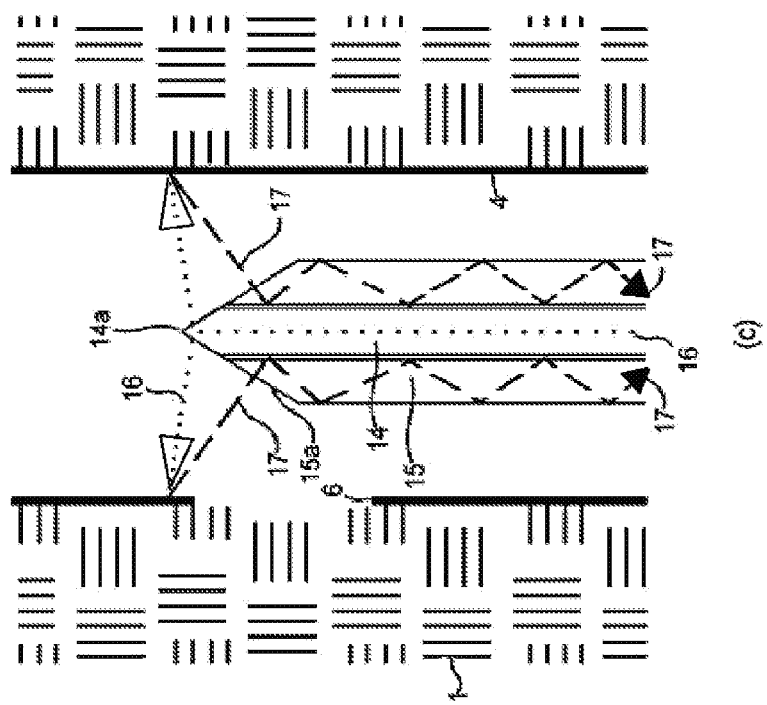
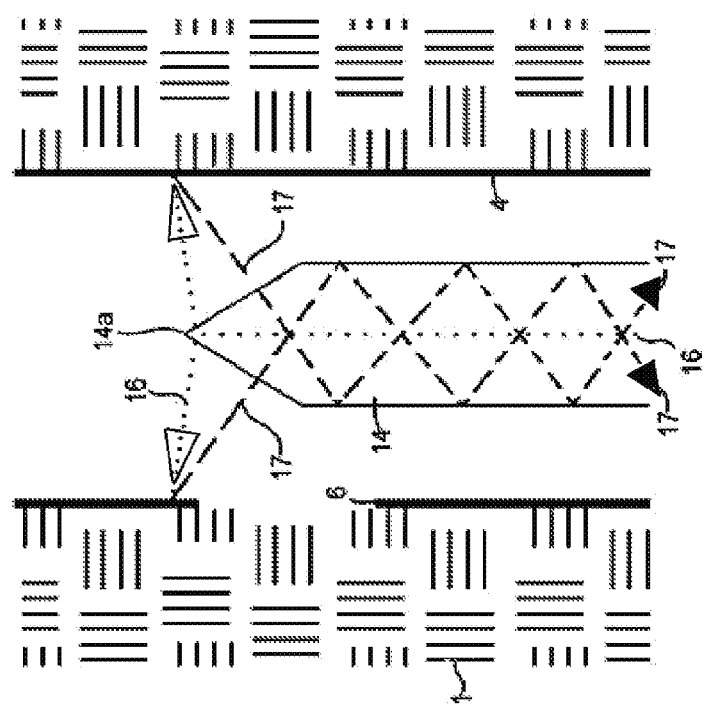
Fig. 1

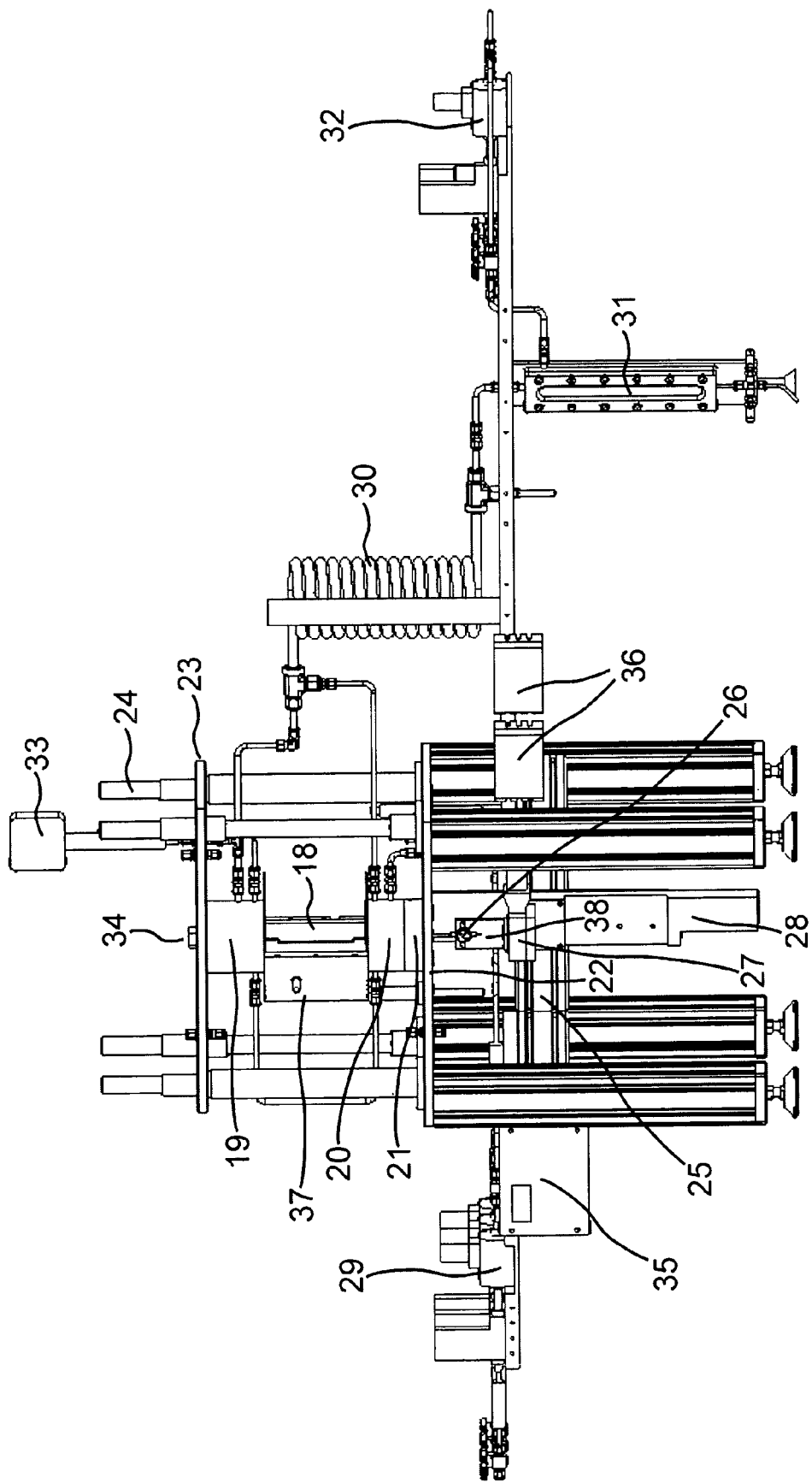

IN-SITU MEASUREMENTS OF SPATIALLY RESOLVED SPECTROSCOPIC DATA WITHIN A REACTOR CHAMBER OF A REACTOR

CROSS-REFERENCE TO RELATED APPLICATIONS

This application is the U.S. National Phase application of PCT International Application No. PCT/EP2009/008973, filed Dec. 15, 2009, the disclosure of which is incorporated herein by reference in its entirety for all purposes.

FIELD OF THE INVENTION

The invention relates to a reactor comprising a reactor chamber and a device for collecting spectroscopic information comprising a light guiding capillary and/or light guiding fiber in which a portion of the light guiding capillary and/or light guiding fiber is situated inside the reactor chamber. Further, the invention relates to a method for analyzing a reactor state.

BACKGROUND OF THE INVENTION

Reactor measurements are central to heterogeneous catalysis research. Apart from reactors which feature a number of discrete sampling points, typically less than ten, all reactor designs have in common that reaction products are analyzed in the reactor effluent stream be it gaseous or liquid. The reaction pathway, i.e. how the reactants are transformed into products remains hidden and only a single kinetic data point is obtained for a set of reaction variables. In addition to kinetic information, heterogeneous catalysts are often characterized spectroscopically to investigate their geometric and electronic structure, surface species and active sites. As a catalyst is a dynamic system and adapts to its chemical environment, in situ spectroscopic techniques become more and more important in heterogeneous catalysis research. These techniques aim at bridging the material and pressure gap by studying polycrystalline powders or supported catalysts under working reaction conditions.

U.S. Pat. No. 4,676,955 discloses an instrument to measure catalytic reaction rates. The reactor is built on the recycle reactor principle and has an internal recycle blower that is floating on a feed fluid. The recycle blower creates a large internal recycle flow and thereby eliminates all internal temperature and concentration fluctuations. During operation of the reaction vessel the catalyst is inserted into a catalytic basket situated inside the reaction vessel. After placing the catalytic basket inside the reaction vessel, the vessel is closed and then flushed with an inert gas, such as nitrogen, to remove all air and undesirable reactive gases contained therein. A feed gas is then fed into the reaction vessel until a desirable pressure is obtained. Further, the reaction vessel is heated until a temperature reaches a desirable range for the specific reaction to be analyzed. Once a desirable pressure and temperature has been reached, the reaction is allowed to continue for a suitable amount of time. During the reaction period, the fluid in the upper portion of the vessel cavity is drawn downwardly through the catalyst bed by impeller vanes and then outwardly to the side of the bottom portion of the cavity. The fluid is then forced upwardly and once again is drawn downwardly into the catalyst bed. Such recycling continues throughout the reaction with a small amount of product being removed through an outlet port for analysis. The mean cover of the reaction vessel is equipped with a desirable number of ports to accommodate various desired functions. Thus, a thermocouple may extend into the catalytic bed portion of the reaction vessel to measure the temperature therein.

M. Bosco, F. Vogel, Catalysis Today, 116 (2006) 348-353, describe an optically accessible channel reactor for the kinetic investigation of hydrocarbon reforming reactions. The reactor allows surface temperature measurements along the reactor through a quartz window using IR thermography. The catalyst is coated as a thin layer onto a metal plate placed at the bottom of the reactor channel. The massive metal body of the channel reactor may be heated by heating cartridges such that a uniform temperature distribution along the channel can be maintained. A small stream of gas can be withdrawn with a moveable capillary to measure the concentration profile in the reactor. The catalyst surface temperature is measured using an infrared camera. By using a quartz glass window the spectral range of the camera has to be in the near infrared region. To take into account the emissivity of the catalyst surface a calibration is performed. A thermocouple is placed in close contact to the catalyst surface and the reactor is heated to different temperatures until the reactor is well thermally equilibrated. A power law is fitted to the data points. After an infrared picture of the catalyst surface is taken, the measured intensities are read out along the center line of the reactor flow direction. The temperature difference is calculated between the measured temperature of the catalyst surface during the reaction and during flushing the reactor with pure argon at a constant setting of the heating system. The disadvantage of the described reactor lies in the fact that radiation heat losses are induced by measuring the temperature from outside through a window affecting indirectly flow and surface chemistry compared to an insulated reactor.

R. Horn, K. A. Williams, N. J. Degenstein, L. D. Schmidt, Journal of Catalysis 242 (2006) 92-102 investigated the mechanism of catalytic partial oxidation of $CH_4$ on Rh-coated $\alpha$-$Al_2O_3$ foam monoliths by measuring species and temperature profiles along the catalyst axis and comparing them with numerical simulations. A thin quartz capillary connected to a quadrupole mass spectrometer is moved through the catalyst with a spatial is resolution of about 0.3 mm. The reaction is carried out in a quartz tube. High-purity reactants $CH_4$, $O_2$ and the internal standard Ar are fed through calibrated mass flow controllers through a side port at the bottom of the tube and leave the reactor from the top for incineration. An injection needle inserted through a septum at an end port at the bottom of the tube enables guided movement of the capillary without noticeable gas losses. $\alpha$-$Al_2O_3$ foams loaded with Rh are used as catalysts. To avoid axial radiative heat losses in the reaction tube, two uncoated $\alpha$-$Al_2O_3$ foams are used as heat shields. To avoid bypassing of gas, the catalyst and the heat shields are tightly wrapped in alumo-silicate paper. The reaction profiles are measured by sliding a 20 cm long fine quartz capillary through a channel, diamond drilled through the centerline of the catalyst. The lower end of the capillary is connected to a ported micro volume tee. The opposite port is used to feed a thermocouple into the capillary. The tip of the thermocouple is aligned flush with the open end of the capillary to measure species composition and temperature simultaneously at each point in the catalyst. The side port of the tee is connected to a stainless steel capillary, which is inserted into the inlet valve of a mass spectrometer vacuum chamber. At the end of the stainless steel capillary, a rotary vane pump generates a vacuum of about 500 mTorr, forcing a permanent flow from the end of the quartz capillary positioned in the catalyst to the sapphire seat of the MS inlet valve. The tee is mounted on a micrometer screw so that the capillary can be moved up and down with sub-millimeter resolution. All profiles are measured by sliding the capillary tip down (i.e., against the flow direction) from a position 3 mm downstream to the end of the catalyst through the catalyst up to about 5 mm into the front heat shield. Using this technique, the open channel is left downstream of the capillary tip and does not influence the sample composition at the tip position.

In a further paper, Journal of Catalysis, 249 (2007) 380-393, R. Horn, K. A. Williams, N. J. Degenstein, A. Bitsch-Larsen, D. Dalle Nogare, S. A. Tupy and L. D. Schmidt describe a modified reactor and capillary sampling system. The sampling capillary comprises a side sampling orifice and a thermocouple aligned with the sampling orifice. The quartz sampling capillary and thermocouple meet in a stainless steel tee, the third port of which is connected to a stainless steel capillary that discharges into the inlet valve of a mass spectrometer. A pump generates a vacuum at the end of the stainless steel capillary, forcing the gases from the sampling orifice into the mass spectrometer. Moving the capillary/thermocouple assembly up and down allows measuring species and temperature profiles along the centerline of the catalyst. The measured temperature is a gas temperature as the thermocouple is in thermal contact with the flowing gas but not with the catalyst surface. The reaction cell is self-supported on a steel mounting frame with stainless steel inlet and outlet tubes. The sampling capillary is guided in steel capillary liners to avoid any bending leading to uncertainties in the sampling orifice position. The compact and rigid self-supported construction of the reactor provides precise geometric alignment and is easy to dismantle and reassemble. The capillary is moved by a stepper motor mounted underneath the reactor. This allows automatization of the experiment such that larger experimental campaigns may be conducted.

To understand heterogeneous catalysis in more detail it is desirable to follow in situ how the reactants are transformed into products and how the catalyst changes along the reaction coordinate. Although it has been demonstrated that spatially resolved measurements of gas species and temperature may be performed in situ inside a reactor, the catalyst has been treated so far as a black box.

The problem underlying the invention therefore is to provide a reactor design that enables in situ monitoring of a sample, e.g. a catalyst, in a reactor under working conditions. The reactor design should also monitor changes of the fluid species (gas or liquid) and solid and fluid temperature measurements.

SUMMARY OF THE INVENTION

The reactor according to the invention is equipped with a device for collecting spectroscopic information. The device includes a light guiding capillary and/or light guiding fiber having a portion situated inside the reactor chamber and, therefore, allows collecting information directly from a sample placed inside the reactor chamber without any disturbances introduced by optical sampling ports, e.g. a window. Spectroscopic information allows in situ monitoring of the sample, e.g. a catalyst, and an interpretation of the geometric and electronic structure of the catalyst as well as an in situ investigation of active sites or surface species bound to the catalyst.

Spectroscopic information is understood to be information on intensity and/or frequency of electromagnetic radiation emitted, absorbed, reflected or scattered by a sample. Spectroscopic information may be obtained at a particular energy level, e.g. the intensity of an emission, absorption or scattering of electromagnetic radiation at a particular wavelength. Preferably, however, spectroscopic information is obtained within a particular range of energy, e.g. a particular wavelength range, such that an intensity of emission, adsorption, reflection or scattering is determined dependent on the energy, i.e. frequency, of the corresponding electromagnetic radiation, such that a spectrum may be obtained. The spectroscopic information is preferably collected by optical spectroscopy.

Basically every type of reactor may be equipped with the device for collecting spectroscopic information to obtain a reactor according to the invention. A reactor is understood as an apparatus comprising a reaction chamber in which a process may be performed during which process at least one alteration of a parameter takes place that can be measured by a spectroscopic method, in particular an optical spectroscopic method. Such reactor may be a reactor for performing a chemical process, in particular a chemical synthesis, or may be a reactor for performing physical processes, mixing of several components or grinding a solid component. An exemplary mixing process is compounding of polymers. However, the term "reactor" also comprises apparatuses used e.g. in food production wherein in such apparatus a cooking or baking process is monitored by a spectroscopic method.

BRIEF DESCRIPTION OF THE DRAWINGS

FIG. 2: an illustration of a device used for performing the experiments;

FIG. 3b: a magnified view of the tip of the light guiding fiber inserted in a light guiding capillary of FIG. 3a;

Figure 10:
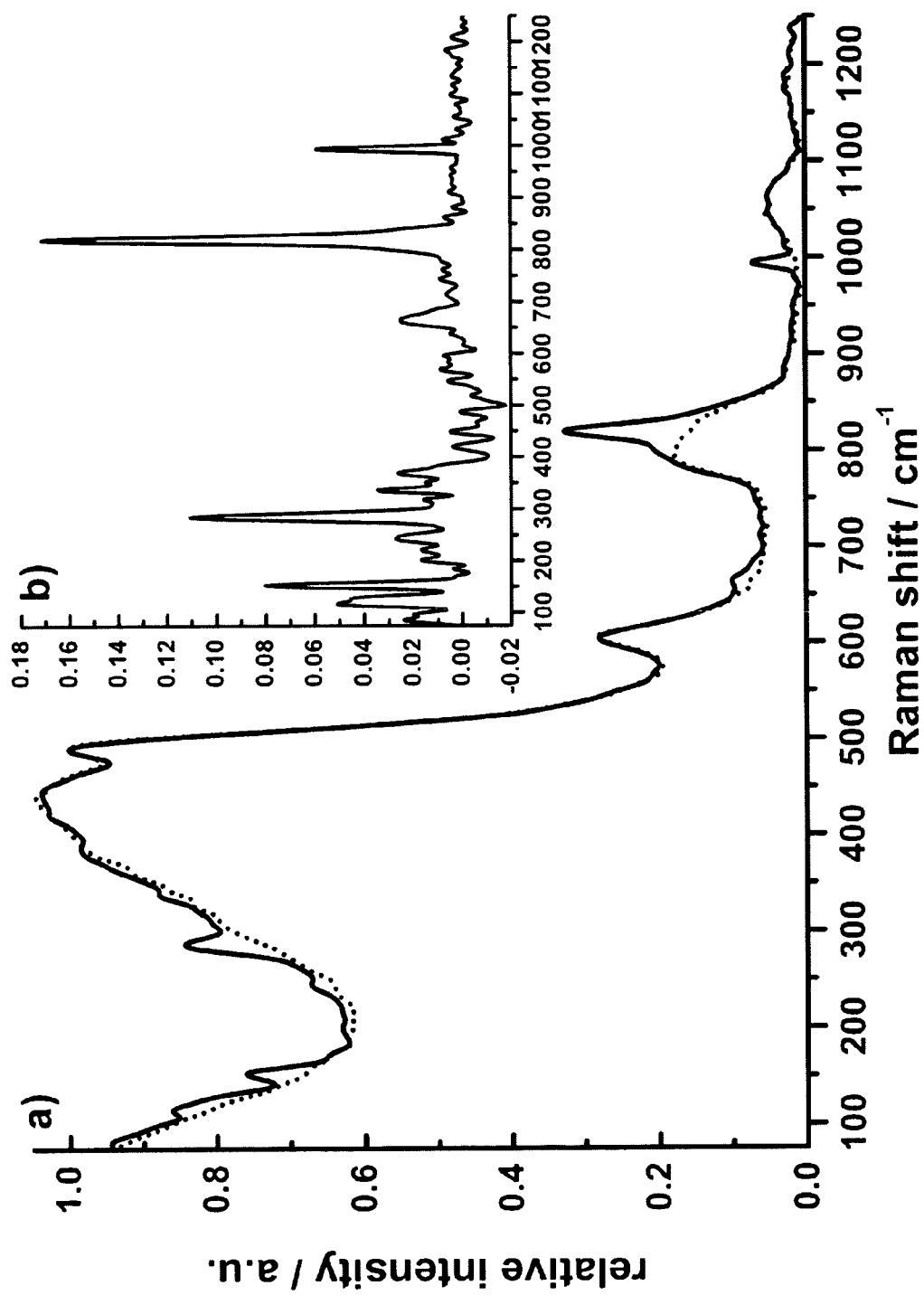

FIG. 10: Raman spectra measured with a sensor including a light guiding fiber inserted into a light guiding capillary inside the sampling capillary placed in a catalyst bed composed of 30 wt % MoO$_3$ supported on α-Al$_2$O$_3$ spheres. Blank spectrum of the tip of the light guiding fiber outside the catalyst bed (dotted line) and spectrum of the tip of the light guiding fiber inside the catalyst bed (solid line) showing additional peaks due to MoO$_3$. Insert: Raman spectrum of MoO$_3$ calculated as difference from spectrum inside the catalyst bed—the blank spectrum of the sensor.

DETAILED DESCRIPTION OF THE INVENTION

According to a preferred embodiment, the reactor is a reactor used to perform chemical reactions.

According to a particularly preferred embodiment, the reactor is designed as a flow reactor through which are transported fluid reaction components in gaseous or liquid form. The reactor may take the form of a packed-bed reactor or may be a type of column reactor. However, the reactor may also be a type of batch reactor, e.g. a stirred tank reactor. Basically, no particular restrictions apply to the type of reactor.

The reactor comprises a reactor chamber in which chemical reactions or physical processes are intended to take place, such as transport of heat and mass. The reaction chamber may be filled with a solid phase, e.g. with a catalyst which may be fixed to a solid carrier. The reactor may be of the type of a fixed-bed reactor or of a fluidized-bed reactor. According to a preferred embodiment, the solid phase comprising the carrier and/or the catalyst is provided in the form of a monolith. The monolith may comprise parallel channels, e.g. having a hexagonal cross section, or may have the form of a reticulated foam. A suitable refractory material that may be used as a carrier is α-Al$_2$O$_3$. Preferably, the catalyst is coated on a suitable carrier. However, a solid catalyst may also be coated directly to the surface of a wall of the reaction chamber.

According to the invention a device for collecting spectroscopic information may include a light guiding capillary and or light guiding fiber inserted in a sampling capillary disposed inside the reaction chamber. A light guiding capillary and/or light guiding fiber may be used by the device for collecting and processing spectroscopic information, in particular for collecting electromagnetic radiation emitted, absorbed, reflected or scattered by a sample, preferably optical radiation. The collected spectroscopic information may be guided to a place outside the reactor chamber for further processing. The sampling capillary may be situated inside the reaction chamber, e.g. close to the center of the reaction chamber or may be placed close to an outer wall of the reaction chamber. Preferably, the sampling capillary is placed at a location inside the reaction chamber at which the reaction conditions will be representative for a chemical reaction or physical process performed inside the reaction chamber. When using a reactor equipped with a solid catalyst placed on a carrier for performing a heterogeneously catalyzed reaction, the sampling capillary preferably will be placed in close proximity to the surface of the solid catalyst, preferably at a symmetry line of the catalyst bed, e.g. the center of the catalyst bed. This allows obtaining spectroscopic information on processes occurring on the catalyst surface or processes influencing the catalyst structure.

The light guiding fiber and/or light guiding capillary within the sampling capillary preferably is connected to a device for processing and displaying the spectroscopic information collected inside the reaction chamber, preferably situated outside the reactor chamber. Such device may be a spectrometer, spectrograph or computer for processing the data collected by the sensor, or may be a display or a chart recorder for displaying the spectroscopic information. A suitable connection, e.g. a fiber, may then be used to transfer the spectroscopic information from the device to a computer for further processing.

The device may be designed for only collecting electromagnetic radiation emitted from a sample inside the reaction chamber. However, according to an embodiment, the device for collecting spectroscopic information may be combined with a radiation source for exciting a sample inside the reaction chamber. For this purpose, a light source may be placed close to the device and the sample may be irradiated by light from the light source. The sample is excited by appropriate radiation, e.g. through a laser light source. The excited sample may then emit, absorb, reflect or scatter electromagnetic radiation that is collected by the device as spectroscopic information.

According to an embodiment, the sample is illuminated by laser light of a defined wavelength which is scattered by the sample. The elastically and inelastically scattered light will then be collected by the device. In this embodiment, the inelastically or the elastically scattered light may then be used for in situ analysis of processes occurring inside The reactor chamber, e.g. by means of Raman spectroscopy. The device may act as a light source as well as a collector of spectroscopic information. However, it is also possible to provide a separate radiation source and to use the device only for collecting spectroscopic information.

According to a preferred embodiment, the device for collecting spectroscopic information comprises at least one optical radiation guide for collecting optical radiation emitted, absorbed, reflected or scattered by a sample and at least one optical radiation guide for guiding radiation onto the sample for excitation. This allows placement of equipment used for analyzing the optical radiation emitted, absorbed, reflected or scattered by a sample or for generating light to excite the sample outside of the reactor. The optical radiation guide for collecting optical radiation emitted, absorbed, reflected or scattered by a sample and the optical radiation guide for guiding optical radiation onto the sample for excitation may be combined or may be provided as separate devices.

An optical radiation guide is understood to be a medium that is transparent to optical radiation collected from a sample or used for excitation of a sample and may transmit the optical radiation to or from the sample from or to a distant place, e.g. outside of the reactor.

According to an embodiment, at least one of the group formed by the at least one optical radiation guide for collecting optical radiation emitted, absorbed, reflected or scattered by a sample and of the at least one optical radiation guide for guiding optical radiation onto the sample for excitation has the form of a fiber. The fiber is transparent to optical radiation collected from a sample and to optical radiation used for excitation of the sample.

The device may according to an embodiment comprise a fiber transparent to light used for excitation and to light emitted, absorbed, reflected or scattered by the sample. The device may then serve both functions, i.e. may be used for excitation of a sample as well as for collecting spectroscopic information. For example, light emitted from a laser source may be guided by the transparent fiber to the sample, such as a solid catalyst placed in the reactor chamber and scattered by the sample. The same fiber may also collect light emitted from the sample. Excitation of the sample and collection of spectroscopic information may take place simultaneously or consecutively.

However, according to an embodiment, a device may be used for excitation of a sample and for collecting spectroscopic information, e.g. by using separate transparent fibers for each purpose.

According to an embodiment, the device for collecting spectroscopic information includes a bundle of fibers. Some of the fibers may be used to distribute electromagnetic radiation to a sample for excitation and some of the fibers may be used to collect electromagnetic radiation emitted, absorbed, reflected or scattered by the sample.

According to a preferred embodiment, optical spectroscopy is used for analyzing the collected spectroscopic information. Preferably, electromagnetic radiation in a range covered by infrared, near infrared and ultraviolet/visible radiation is the collected spectroscopic information. Preferably radiation of a wavelength within a range of about $10^{-7}$ to $10^{-3}$ m is the collected spectroscopic information. According to a preferred embodiment, the collected spectroscopic information is detected by a sensor selected from the group of IR-, NIR-, UV/Vis-, Raman- and fluorescence sensitive sensors.

The reactor according to the invention allows in situ analysis of processes occurring inside the reactor, i.e. under actual reaction conditions without disturbance, e.g. heat losses, induced by an optical sampling port, such as a window.

According to an embodiment, it is preferred that those parts of the device used for collecting spectroscopic information are placed inside the reactor chamber, whereas devices used for processing the collected spectroscopic information are placed outside the reactor.

According to a preferred embodiment, the device for collecting spectroscopic information comprises at least one fiber located inside a capillary wherein one of the fiber and the capillary acts as radiation guide for collecting radiation emitted, absorbed, reflected or scattered by a sample and the other acts as radiation guide for guiding radiation onto the sample for excitation.

Accordingly, light used for excitation of the sample may be guided to the sample through the fiber from a laser source and light emitted, absorbed, reflected or scattered by the sample is collected by the capillary and guided towards a device for analysis. The same configuration can also be used in reverse order, i.e. irradiation through the light guiding capillary and collection of emitted, absorbed, reflected or scattered light by the fiber located inside the capillary. Preferably, light for excitation of the sample is guided through the fiber and light collected from the sample is guided through the capillary.

A single combination of a fiber situated inside a capillary may be used. According to an embodiment, a bundle of such combinations may be used for collecting spectroscopic information. The bundle comprises at least two, according to an embodiment from 4 to 20 combinations of a fiber sitting inside a capillary.

According to this embodiment, the device for collecting spectroscopic information is composed of a fiber located inside a light guiding capillary and radiation for spectroscopic analysis is emitted from the fiber tip and collected after interaction with the sample by the light guiding capillary or vice versa. Fiber and capillary are transparent for radiation used to excite the sample as well as for radiation emitted, absorbed, reflected or scattered by the sample and collected by the device. A transparent fiber/capillary allows collecting information with minimum requirements for space and the device may be placed very close to a sample, e.g. a catalyst surface. Further, a fiber/capillary allows a very easy transfer of the collected spectroscopic information to a device placed outside of the reactor were the collected information may be processed. Further, a fiber/capillary may be designed flexible such that the fiber may easily be placed inside the reactor chamber. The fiber and the light guiding capillary may have very small diameters.

According to an embodiment the diameter of the fiber is less than 1 mm, according to a further embodiment is less than 600 µm and according to a further embodiment is less than 500 µm. The fiber may have a diameter of only few 100 µm. According to an embodiment, the diameter of the fiber is at least 10 µm, according to a further embodiment at least 100 µm. The fiber may comprise a single fiber or may be a bundle of fibers. Some of the fibers may be used for transmitting light for excitation of the sample whereas others may be used to collect radiation emitted, absorbed, reflected or scattered by a sample inside the reactor chamber and to guide the light to a device for processing. When using a fiber bundle, the outer diameter of the individual fibers may be selected within a range of down to about 10 µm.

When using a combination of a fiber sitting inside a capillary, the inner diameter of the light guiding capillary is chosen to match closely the outer diameter of the inner fiber or the inner fibers being used. The thickness of the capillary wall preferably is selected within a range of 10 µm to 500 µm, more preferred 50 µm to 200 µm.

The fibers or capillaries making up the optical device are made of a material transparent to the radiation emitted by a sample and used to collect spectroscopic information. A suitable material is fused silica that also may be doped with a suitable dopant to increase transparency of the fiber. Another suitable material is sapphire. Also photonic crystal fibers are suitable.

The individual fibers of a fiber bundle may be arranged in any order but preferably are arranged in circular closed package. According to an embodiment, the fiber bundle takes the form of a circular closed package at its end located inside the reactor chamber whereas at the other end the fiber bundle is separated into individual fibers which are connected to a radiation source or a device for analyzing and processing the collected spectroscopic information. In an analogous manner also a combination of a fiber sitting inside a capillary may be used in the form of a bundle.

The device preferably comprises a tip and the spectroscopic information is preferably collected at the tip of the device.

When collecting spectroscopic information inside a reactor it may be of interest for some embodiments to exactly know the site where the spectroscopic information is collected. This is of particular interest in a reactor in which reaction conditions differ depending on the position within the reactor, e.g. in a flow reactor. According to an embodiment, a device is used that receives spectroscopic information from a limited and well defined area of the sample.

According to an embodiment, the fiber used to collect spectroscopic information is beveled at its tip located inside the reaction chamber. According to a preferred embodiment, the fiber tip takes the form of a cone. By suitably adjusting the cone angle at the tip of the fiber it is possible to select an angle relative to the fiber axis in which light is emitted from and collected by the device. According to an embodiment, the cone angle of the fiber tip is selected, such that light used for exciting a sample leaves the fiber tip at an angle about perpendicular to the fiber axis. The angle between the fiber axis and the direction of the light emitted by the fiber for excitation of the sample is preferably selected within a range of 80 to 90 degrees.

Since light collected at the fiber tip takes about the same route as light scattered by the fiber, although in opposite direction, spectroscopic information collected by the fiber stems from a defined and limited area inside the reaction chamber.

According to a particular preferred embodiment, the optical device for irradiation of the sample and collection of the spectroscopic information consists of a fiber located inside a light guiding capillary. Both ends of fiber and light guiding capillary located inside the reactor are beveled to emit and collect light at a defined angle to the fiber axis.

The ends of the fiber and the light guiding capillary can be aligned or displaced from each other by a defined distance. According to the latter embodiment the fiber projects from the tip of the capillary.

According to an embodiment, the ends of the fiber and the light guiding capillary outside the reactor are longitudinally distant from each other to allow independent acceptance of light from an external light source and collection of the light emitted or scattered by the sample.

In a reactor with inhomogeneous reaction conditions, e.g. a flow reactor, it is of particular interest to obtain spatially resolved spectroscopic information from inside the reactor chamber. This allows recordation of a reaction profile along a longitudinal axis of a reactor, i.e. in or against the direction of fluid flow.

According to an embodiment, the light guiding capillary and/or light guiding fiber is arranged moveably inside the reactor chamber, in particular is movable parallel to an axis of the reactor, preferably a longitudinal axis of the reactor. For example, for investigating reaction processes occurring in a flow reactor, it is preferred to move the device in the direction or against the direction of the fluid flow to obtain a reaction profile. The movement of the device preferably is performed with high precision and in small steps, e.g. manually by a micrometer screw or by a motor or by a step motor. When using a motor for moving the device inside the reaction chamber, collection of spectroscopic data may be automated.

According to a further embodiment, the light guiding capillary and/or light guiding fiber is rotatable around its longitudinal axis. A catalyst bed may be inhomogeneous, e.g. when using a reticulated foam as a carrier for the catalyst. By rotating the device around its longitudinal axis, such inhomogeneity will be averaged. This is of particular interest when using the device for collecting spectroscopic information together with other types of sensors.

According to an embodiment, the device for collecting spectroscopic information is combined with at least one temperature-sensitive sensor. This combination allows obtaining spectroscopic information from a particular site inside the reactor chamber and at the same time to measure the temperature at this reaction site. Preferably, the light guiding capillary and/or light guiding fiber and the at least one temperature sensitive sensor are arranged in close proximity to each other such that the corresponding information originates from the same place inside the reaction chamber.

Depending on the type of temperature sensitive sensor used, it is possible to obtain information on the temperature of the catalyst, i.e. on the stationary phase, or on the temperature of a gas or liquid phase, i.e. the mobile phase. When using a thermocouple, the temperature sensitive sensor is in direct contact with fluid. This allows determination of the temperature of the fluid phase. When using a pyrometer fiber as a temperature sensitive sensor, thermal radiation emitted from a catalyst surface can be collected and transformed into a temperature of the solid using a pyrometer. The pyrometer is preferably operated in quotient mode as the emissivity of the catalyst bed might change along the profile coordinate.

When using a beveled fiber tip of a distinct cone angle, light emitted from the fiber is distributed in a direction having a defined angle relative to the fiber axis. Light emitted from the catalyst bed will be collected from the same acceptance angle. This allows spatially resolved temperature measurements, of a catalyst surface when moving the temperature sensitive sensor along a longitudinal axis of the reactor.

According to a particular preferred embodiment the device for collecting spectroscopic information is combined with a device for collecting a sample, such as a sampling capillary, inside the reaction chamber, preferably a sample of the fluid phase. This embodiment allows kinetic measurements on the fluid and the solid phase and optical spectroscopy at the same time wherein the measurements according to an embodiment may be performed in a spatially resolved manner.

The sampling capillary preferably is arranged in close proximity to the light guiding capillary and/or light guiding fiber such that information obtained by the device for collecting spectroscopic information may be correlated to kinetic data deduced from analysis of the collected samples. The sampling capillary preferably is connected to an analytical device that allows qualitative and/or quantitative analysis. For analysis the sample may be transferred to a mass spectrometer, a gas chromatograph or an HPLC-apparatus.

According to a preferred embodiment the sampling capillary inside the reactor chamber comprises an orifice for sample collection. The sampling capillary preferably has an inner diameter of less than 3 mm, according to a further embodiment of less than 2 mm, according to a still further embodiment of less than 1 mm. The sampling capillary preferably is made of a material that is inert under the reaction conditions present in the reaction chamber. According to a particularly preferred embodiment, the sampling capillary is made of a material transparent to electromagnetic radiation emitted, absorbed, reflected or scattered by a sample and collected by the sensor for collecting spectroscopic information. According to an embodiment, the material is transparent to UV/VIS, NIR and/or IR-radiation. A suitable material for the sampling capillary is fused silica.

The sampling capillary has an orifice for collecting a sample. The sample may be transported through the capillary by a pressure gradient between the reactor chamber and the end of the capillary situated outside the reactor chamber.

According to a preferred embodiment, the orifice for collecting a sample is situated at a sidewall of the sampling capillary, preferably distant from a closed end of the sampling capillary. The diameter of the orifice depends on the size of the sampling capillary and preferably is less than 200 µm and according to an embodiment is within a range of 50 to 150 µm.

According to an embodiment, the distance between the closed end of the sampling capillary and the orifice located in the sidewall of the sampling capillary is selected, such that the end of the sampling capillary remains seated within a bearing when the orifice is in a position corresponding to the maximum deflection of the sampling capillary. Such bearing may be formed by a channel drilled inside the catalyst bed.

In a particularly preferred embodiment, the light guiding capillary and/or light guiding fiber is arranged inside the sampling capillary used for collecting a sample inside the reactor chamber. When providing a transparent fiber or a fiber sitting inside a light guiding capillary, these optical components may be guided through the interior space of the capillary. A small can is formed between the outer wall of the optical component and the inner wall of the sampling capillary which allows transportation of the collected sample to a corresponding device for analysis. The gap preferably has a width of at least 50 μm and according to an embodiment is selected within a range of 100 to 500 μm.

According to a further preferred embodiment, the device for collecting spectroscopic information includes a fiber or of a fiber located inside a light guiding capillary and the tip of the fiber is arranged at a position corresponding to the orifice provided in the sampling capillary for sample collection. The device may comprise a single fiber or a single combination of a fiber sitting inside a capillary or may have the form of a bundle of fibers or a bundle of capillaries with a fiber located in the interior of the capillary. This arrangement allows an immediate correlation of the spectroscopic information and the composition of a sample collected at the same position. When using an arrangement wherein the light guiding capillary and/or light guiding fiber is situated in the interior of the sampling capillary, the sampling capillary is preferably formed from a material transparent to radiation used for collecting spectroscopic information.

For spatially resolved collection of spectroscopic information, as well as of other data, e.g. temperature or composition of the fluid phase, it is advantageous that the device is moved with high precision inside the reactor, preferably without causing pressure losses. According to an embodiment, the sampling capillary for collecting a sample is guided in a liner, e.g. a stainless steel liner. The length of the liner is selected to allow a secure guidance of the capillary and to avoid deflection of the capillary when sliding the capillary up and down.

According to an embodiment, the length of the liner is at least 30 mm and is selected according to a further embodiment within a range of 50 to 200 mm. The inner diameter of the liner is selected such that the capillary fits neatly into the liner still allowing up and down movement of the capillary. The liner is fixed to a suitable support to allow relative movement of capillary and liner. High viscous grease may be used to fill the gap between liner and capillary and to alleviate sliding of the capillary.

According to an embodiment, two liners are used each mounted to a suitable support. Between both liners is left an open space and this space is located in a reservoir for high viscous grease. When the sampling capillary is moved along its longitudinal axis, its outer surface picks up a thin grease layer. The annular gap between the capillary and the liner has a width of few micrometers, preferably less than 50 μm, more preferably of less than 40 μm. Even at high operation pressure in the reaction chamber the high viscous grease therefore will not be squeezed through the annular gap. On the other hand, the grease allows slow movement of the capillary with minimum force as the pressure difference exerts only small forces.

The reactor according to an embodiment comprises a solid catalyst bed inside the reaction chamber. In a particular embodiment, the solid catalyst is formed from one or several reticulated solid foams. To guide the movement of the light guiding capillary and/or light guiding fiber, in particular in an embodiment when the optical component is inserted into a sampling capillary for collecting samples, a channel is preferably provided in the solid catalyst, preferably solid foam, to accommodate the device and/or the capillary. The annular gap formed between the channel wall and the capillary/device preferably is narrow to avoid bypassing of fluid phase and preferably has a width of less than 100 μm.

According to a further aspect the invention is directed to a method for analyzing a reactor state comprising the steps:

Providing a reactor as described above;
Collecting a spectroscopic information from a sample inside the reactor chamber; and
Processing said collected spectroscopic information.

The reactor described above is in particular suited for in situ investigation of a reaction performed inside the reactor. It allows obtaining information on a structure or electronic state of a component involved in the reaction at a particular site inside the reactor chamber. As already described above, electromagnetic radiation emitted from a sample may be collected to be displayed in appropriate form, in particular in the form of a spectrum. The electromagnetic radiation may be emitted directly by a sample inside the reactor or may be collected after suitable excitation of the sample, e.g. by irradiation of the sample by light, e.g. laser light. Preferably, optical spectroscopy is used to collect spectroscopic information. A suitable exemplary method for collecting spectroscopic information is Raman spectroscopy. Light of particular wavelength, e.g. laser light, is directed onto a sample and inelastically scattered light is collected as spectroscopic information. However, other spectroscopic methods may be used as well. Suitable methods are UV/VIS-spectroscopy, NIR-spectroscopy, IR-spectroscopy, and fluorescence spectroscopy.

According to an embodiment, the method according to the invention allows spatially resolved optical spectroscopy directly at a reaction site inside the reactor. By the method according to the invention detailed information on processes occurring inside the reactor may be obtained. In particular it is possible to obtain a reaction profile by moving the sensor along a defined pathway in the reaction chamber.

According to an embodiment the spectroscopic information is collected at a first position inside the reactor chamber to obtain a first data set, preferably in the form of a spectrum. Spectroscopic information is then collected at least at one further position inside the reactor chamber to obtain at least a second data set, preferably in the form of a spectrum. The device may then be moved to a third position, as well as to further positions inside the reactor, wherein at each position spectroscopic information is collected. By following a defined movement program, the method according to the invention allows a detailed interpretation of processes occurring inside the reactor.

According to a further embodiment, information obtained by collecting spectroscopic information with the device may be combined with temperature measurements. As already described above, a thermocouple may be used to measure the temperature of a fluid transported inside the reactor. According to another embodiment, a properly beveled pyrometer fiber may be used to collect thermal radiation emitted from a sample inside the reactor chamber, such as from a catalyst, and transformed into a catalyst temperature using a pyrometer.

In a particularly preferred embodiment, optical spectroscopy is combined with collection of a sample inside the reaction chamber which sample may then be analyzed for its composition. This allows combination of e.g. kinetic measurements and optical spectroscopy. Such measurements may also be performed in a spatially resolved manner as has been described above.

According to a most preferred embodiment of the method according to the invention, temperature measurement and sample collection is performed in such way that all data may be linked to a defined position inside the reactor chamber. To allow correlation of the information obtained, the temperature is preferably determined and/or the sample is collected at a place inside the reactor chamber located in close proximity to the site for collecting spectroscopy information inside the reactor chamber.

FIG. 1a schematically shows a section of the setup of the interior of a catalyst chamber in which is situated a moveable device for collecting spectroscopic information as well as other information, in particular information on kinetic data and on temperature. A catalytic reaction is conducted in a flow reactor containing a catalyst bed 1 sandwiched between two inert packings 2. The catalyst bed 1 as well as the packings 2 may be formed by reticulated refractory foams, e.g. $\alpha$-$Al_2O_3$ foams. To obtain catalyst portion 1, the foam may be coated with a thin layer of a catalytically active material according to known methods. The inert packings 2 are used to check in each experiment for activity of the support as well as pre- and post-catalytic chemistry. Through all, catalyst bed 1 and inert packings 2, goes a channel 3 into which a sampling capillary 4 is slidably introduced. The sampling capillary 4 is sealed at the upper end 5. Channel 3 has a diameter slightly larger than the outer diameter of sampling capillary 4, such that sampling capillary 4 fits tightly into channel 3, and may be moved up and down along its longitudinal axis. Only a small gap is formed between sampling capillary 4 and the wall of channel 3 such that bypassing of large amounts of fluid phase through the gap is avoided. Profile of reactants, intermediates and products are measured by moving sampling capillary 4 with micrometer resolution through channel 3. Sampling occurs via a side sampling orifice 6 drilled at such distance from closed capillary tip 5 that no open channel 3 results from moving sampling capillary 4 up and down. In addition to species sampling, capillary 4 may accommodate various other probes, like a thermocouple, a pyrometer fiber, or a device for optical spectroscopy allowing measuring of the fluid temperature, the catalyst temperature and/or spectroscopic information from the catalyst and/or the gas phase. To correlate information about species sampled through side sampling orifice 6 and temperature or spectroscopic information, the temperature or optical device used should be aligned with the side sampling orifice 6 or should be at any other defined position with respect to the side sampling orifice 6. In an arrangement according to the invention a device A can be used comprising a single light guiding fiber 14 (FIG. 1b)) or a device B can be used comprising a single light guiding fiber 14 inserted into a light guiding capillary 15 (FIG. 1c) for collecting spectroscopic information. As shown in FIGS. 1b) and 1c) device A or B can be inserted into the inner space of sampling capillary 4 to allow simultaneous sampling and optical spectroscopy. For analysis of reactor conditions a fluid is directed through the package of catalyst bed 1 and inert packings 2. Arrows 12 and 13 designate the direction of flow of the fluid. Sampling capillary 4 may be slid up and down as indicated by arrow 10 by action of a stepper motor (not shown). Further, sampling capillary 4 may be rotated around its longitudinal axis as indicated by arrow 9.

For kinetic measurements a sample will enter through sampling orifice 6 and will be forced through the gap between sampling capillary 4 and either fiber 14, if device A is used, or light guiding capillary 15, if sensor B is used for collecting spectroscopic information. The sample will then leave sampling capillary 4 at position 11 where sampling capillary 4 has a gap to be transferred to an analytical device, e.g. a mass spectrometer or a gas chromatograph. To force fluid flow in this direction either an overpressure is applied at side sampling orifice 6 or an underpressure is applied at the gap 11 in sampling capillary 4. To direct the fluid flow from the reactor into the analytical device, sampling capillary 4 has to be sealed at location 8.

FIGS. 1b and 1c show in detail a section of sampling capillary 4 into which is introduced either device A composed of a light guiding fiber 14 for collecting spectroscopic information or device B composed of a light guiding fiber 14 inserted in a light guiding capillary 15, respectively. If device A is used, the tip 14a of the light guiding fiber 14 is beveled to allow illumination and light collection perpendicular to the longitudinal axis of the fiber 14. If device B is used both the tip 14a of the light guiding fiber 14 and the front face 15a of the light guiding capillary 15 into which the light guiding fiber 14 is inserted are beveled and aligned to allow separate illumination and light collection perpendicular to the longitudinal axis of fiber 14/capillary 15. The cone angles of 14a and 15a can be different and there can be a fixed distance between 14a and 15a; however, typically 14a and 15a have the same angle and are aligned flush as shown in FIG. 1c. The tip 14a of the light guiding fiber both in optical device A or B is aligned with sampling orifice 6. Sampling capillary 4 is slidably introduced into channel 3. In the embodiment shown in FIG. 1b, the single light guiding fiber 14 for collecting spectroscopic information is also used for excitation of the sample. Incident light 16, delivered, for example by a laser, is guided through fiber 14 and leaves at beveled tip 14a of fiber 14 nearly perpendicular to the longitudinal axis of fiber 14. The angle in which the light is emitted relative to the longitudinal axis of fiber 14 depends on the material of fiber 14, the cone angle and on the wavelength of incident light 16 introduced into fiber 14. The light is then directed onto an area of the catalyst present on the surface of channel 3. The light will excite compounds present in that area and will induce absorption, emission, reflection, or scattering of electromagnetic radiation 17. After interaction with the sample, electromagnetic radiation 17 is then collected at tip 14a of fiber 14 and then will be guided through fiber 14 to a device for processing the spectroscopic information.

In the embodiment shown in FIG. 1c, a device consisting of a light guiding fiber 14 inserted in a light guiding capillary 15 is used for obtaining spectroscopic information from the sample. Incident light 16, which may again be delivered by a laser, for illumination of the sample is guided through light guiding fiber 14 of sensor B and leaves at tip 14a nearly perpendicular to the longitudinal axis of fiber 14. The emission angle is, depending on the material of the light guiding fiber 14, the cone angle and on the wavelength of light 16. Incident light 16 is then directed onto an area of the catalyst present on the surface of channel 3. Incident light 16 will excite compounds present in that area and will induce absorption, emission, reflection or scattering of electromagnetic radiation 17. After interaction with the sample, electromagnetic radiation 17 is then collected at front face 15a of light guiding capillary 15 surrounding the light guiding excitation fiber 14 in device B. The collected electromagnetic radiation will be guided through capillary 15 to a device for processing the spectroscopic information (not shown). As shown in FIGS. 1b) and 1c), incident light 16 used for excitation of the sample and radiation 17 emitted after interaction with the sample uses the same optical pathway in light guiding fiber 14 in device A, but different optical pathways in light guiding fiber 14 and light guiding capillary 15 in device B.

By moving either device A or B along the longitudinal axis, it is possible to perform spatially resolved optical spectroscopy for the characterization of the bed of catalyst 1 and inert packings 2.

Raman spectroscopy is a powerful method for in situ studies in heterogeneous catalysis and has been chosen as a test method, but other optical methods like photoluminescence spectroscopy, UV/VIS-, NIR- and IR-spectroscopy are applicable in a similar manner.

Figure 1:
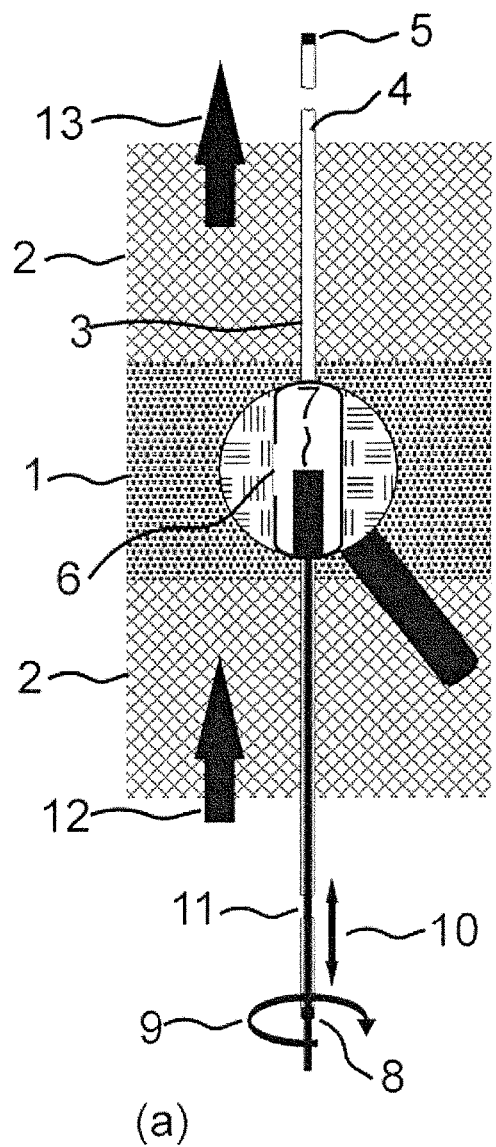
FIG. 1: a) an illustration of an arrangement for measurements of spatially resolved kinetic, temperature and spectroscopic data; b) an illustration of the light pathway if a single light guiding fiber is used; c) an illustration of the light pathway if a light guiding fiber inside a light guiding capillary is used.

FIG. 2 shows a reactor setup as used in the experiments described therein. The reactor is formed of a 200 mm long quartz tube 18 with an inner diameter of 18 mm and an outer diameter of 38 mm meaning a wall thickness of 10 mm. Both ends of the quartz tube 18 which contains catalyst bed 1 and inert packings 2 as shown in FIG. 1 are conically shaped with a cone angle of 20°. For pressure sealing of the reactor tube 18, the cone faces are greased and form fit tightly into an upper and a lower water cooled copper clamp 19 and 20, respectively. The lower copper clamp 20 is mounted to a stainless steel flange 21, which in turn is mounted to a fixed aluminum base plate 22. The upper copper clamp 19 is mounted to a moveable cover plate 23 also made of aluminum. As high axial force, but no lateral force, must be applied to the quartz reactor tube 18, a precise vertical movement of the upper mounting clamp 19 is required. This is accomplished by four linear bearings 24 mounted between cover plate 23 and base plate 22 allowing for precise vertical movements of up to 110 mm. If the reactor is closed and pressurized, 22 springs (0.647 N/mm, not shown) hinged on hooks between base plate 22 and cover plate 23 keep the quartz reactor tube 18 pressure sealed. The entire reactor setup stands on a frame 25 made of material with a cross section of 80×80 mm.

The gas flow through the reactor setup is arranged from left to right and through the reactor tube 18 from bottom to top. At the inlet side, three 6 mm gas pipes are connected to digital mass flow controllers 29 (Bronkorst, type EL-FLOW® equipped with Vary-P valves for large pressure differences). In oxidation catalysis the feed gas is typically composed of an oxidant, like $O_2$ or $N_2O$, a hydrocarbon, like $CH_4$, $C_2H_6$ or $C_3H_8$, and an inert standard, like Ar, He or $N_2$. Therefore, three gases can be mixed using this gas supply. The feed gas mixture enters reactor tube 18 from the bottom, flows through the bed of inerts 2 and catalyst 1 and leaves at the top. After leaving at the top, the reactor effluent gases pass through a tube in a tube heat exchanger 30 to remove all condensable species which are collected in a reservoir 31. Reservoir 31 can be emptied under operation without pressure loss by means of a needle valve. The dry reactor effluent passes through pressure controllers 32 (Bronkhorst, type EL-PRESS®) which expand the gases to atmospheric pressure. For precise pressure measurement in the reactor, a digital pressure gauge (Leitenberger, type TLDMM-A01) 33 is connected close to the outlet of the reactor tube 18.

To heat the catalyst, the quartz reactor tube 18 is surrounded by a split furnace 37 (KANTHAL, type Fibrothal, 450 W, maximum element temperature 1150° C., only one half shown for clarity) connected to a power supply (not shown) and a temperature controller (Eurotherm, model 2416, not shown). The heat transfer between heater and catalyst bed occurs primarily via radiation resulting in a maximum temperature of about 1000° C. without accounting for any heat of reaction. Taking into account that many catalytic oxidation reactions liberate significant amounts of heat, temperatures above 1000° C. can result. For methane oxidation on Pt, the reactor has been successfully operated at temperatures up to 1300° C.

As reacting gas mixtures containing fuel and oxidant under pressure are inherently dangerous, a number of safety measures are taken in designing and operating the reactor. In the first place, feeding of potentially explosive mixtures to the reactor can be excluded by providing upper and lower limits to the mass flow controllers 29 which are outside the flammability limits of the gas mixture. Secondly, the reactor is equipped with a ½" burst disk 34 manufactured and rated to a burst pressure of 45 bar+11−8% (Bormann & Neupert). In case of an explosion, burst disk 34 breaks and releases the pressure instantaneously. In addition to the burst disk, the reactor itself functions like a pressure relief valve, as number and strength of the springs between base plate 22 and cover plate 23 determine the leak pressure of the system. Depending on the application and the target pressure, the spring load can be adjusted to a value slightly higher than the target pressure. This value can be anything between atmospheric pressure and 45 bar. To protect the operator in case of a bursting reactor tube, the ceramic split furnace 37 surrounding the reactor tube is enclosed in a metal housing (not shown). Additionally, the entire reactor is shielded by a safety screen (not shown).

For measurement of high resolution gas species profiles a thin quartz sampling capillary 4 (O.D.=700 µm, I.D.=530 µm) runs through the center of the quartz reactor tube 18 and the packing of inerts 2 and catalyst 1 through channel 3. As already explained with reference to FIG. 1 sampling capillary 4 possesses a small side sampling orifice 6 with a diameter of about 70 µm located at such a distance from the upper, closed end 5 of the capillary 4 that no open channel 3 is left behind when sampling orifice 6 is positioned at the lowest sampling point in the catalyst bed. Keeping the channel 3 filled by the capillary 4 is mandatory to avoid gas bypassing. Details have already been explained with reference to FIG. 1a. The lower open end of the sampling capillary is connected to a 1/16" micro-volume stainless steel cross 26 (Valco), which in turn is connected to a stainless steel holder 38. The stainless steel holder is mounted on a rotary stage 27 and the rotary stage 27 is mounted to a linear stage 28 (both stages from Physik Instrumente GmbH). Both stages are controlled by motor controllers 36. With this arrangement it is possible to move sampling capillary 4 with µm resolution up and down and to rotate it. Rotating sampling capillary 4 is important because some catalyst geometries, e.g. reticulated foam, can have irregular flow patterns and high quality spatial profile measurements will require averaging at different scan lines. To seal the capillary against the outside but still allow movement with minimum force, sampling capillary 4 runs through two 50 mm long stainless steel liners (not shown) with an outer diameter of 1/16" and an inner diameter of 0.03". One of the liners is brazed to lower copper clamp 20 and the other liner is welded to stainless steel flange 21 below the lower copper clamp 20 so that there are a few millimeters open space between both liners. This space is located in a reservoir formed between lower copper clamp 20 and stainless steel flange 21 which contains high viscous silicon grease. If sampling capillary 4 is inserted, its outer surface picks up a thin grease layer. The annular gap between sampling capillary 4 and the steel liners has a width of only 30 µm which is narrow enough that even maximum reactor operation pressure (40 bar) is not sufficient to squeeze the high viscous grease through this annular gap. On the other hand, the grease allows slow movement of sampling capillary 4 with minimum force as the pressure difference exerts only small forces. Gas species sampling is accomplished by means of a transfer capillary (not shown) connecting the micro-volume stainless steel cross 26 with a mass spectrometer (not shown). The transfer capillary is evacuated by means of a membrane pump (not shown) to avoid blocking by condensation of condensable species, e.g. water. A similar arrangement could be used for connecting the sampling capillary with a GC, HPLC, or any other analytical device.

To measure spatially resolved gas and surface temperature profiles, a thermocouple or a pyrometer fiber can be inserted in sampling capillary 4, respectively. If the fiber or the thermocouple tip is aligned with side sampling orifice 6, the measured temperature can be assigned to the respective fluid composition measured at the same location in catalyst bed 1. In case a thermocouple is used, direct thermal contact exists between the sampled gases and the thermocouple tip but no direct thermal contact exists between the thermocouple tip and catalyst bed 1. Therefore, the thermocouple measurement is strongly biased to the actual fluid temperature. In case a properly beveled pyrometer fiber is used, thermal radiation emitted from the catalyst surface can be collected and transformed into a catalyst temperature using a pyrometer 35. The pyrometer should be operated in quotient mode as the emissivity of catalyst bed 1 might change along the profile coordinate.

For optical spectroscopy an optical device can be inserted into sampling capillary 4. As shown in detail in FIGS. 1b) and 1c), respectively, the optical sensor can be for example of type A comprising a single light guiding fiber 14 or of type B comprising a light guiding fiber 14 sitting inside a light guiding capillary 15. In type A the single light guiding fiber 14 is used for both, bringing excitation incident light 16 to the catalyst bed 1 and collecting radiation 17 after interaction with the catalyst. In type B, excitation and collection are spatially separated, such that a single light guiding fiber 14 is used to bring excitation incident light 16 to the catalyst bed 1 and a light guiding capillary 15 is used to collect radiation 17 after interaction with the catalyst 1.

Figure 3B:
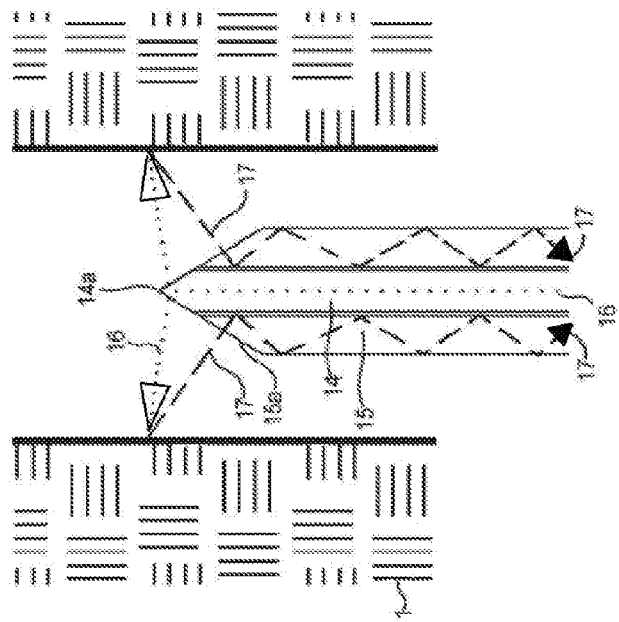
Figure 3A:
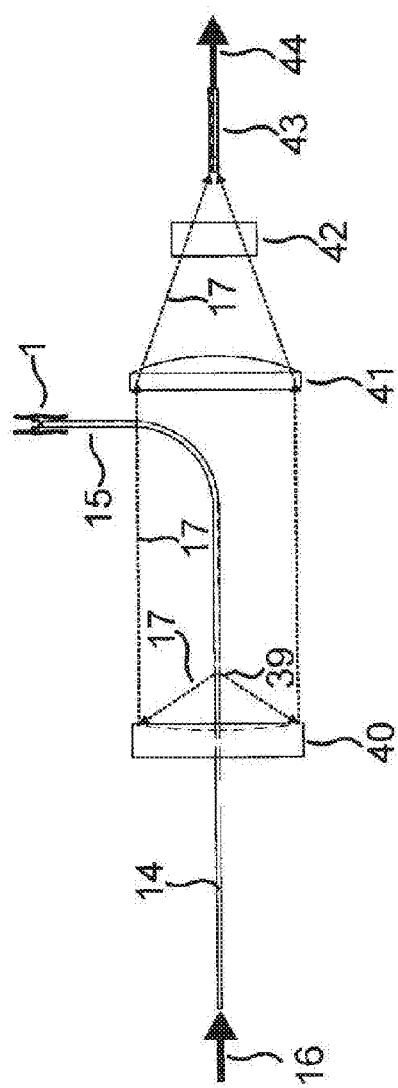
FIG. 3a: a preferred arrangement for coupling light into and extracting light from a light guiding fiber for illumination inserted in a light guiding capillary for collection of light emitted, reflected or scattered inside the reactor and extraction of this emitted, reflected or scattered light for spectral processing.

FIG. 3 shows the operation principle of type B in more detail. Device B comprises a single light guiding fiber 14 located in a light guiding capillary 15. At the end of the sensor B that is located inside sampling capillary 4, as explained with reference to FIG. 1, the beveled tip 14a of the light guiding fiber 14 and the beveled front face 15a of the light guiding capillary 15 are aligned. Both 14a and 15a are beveled for an acceptance angle nearly perpendicular to the longitudinal axis of sensor B. The light guiding capillary 15 is of shorter length than the light guiding fiber 14, so that the light guiding fiber 14 sticks out from the end of light guiding capillary 15. Excitation incident light 16 is introduced into light guiding fiber 14 of device B, travels through fiber 14, and leaves fiber 14 at its tip 14a in an angle almost perpendicular to the longitudinal axis of fiber 14 (FIG. 1c). After interaction with catalyst 1, radiation 17 is collected by the beveled tip 15a of light guiding capillary 15 and travels to end 39 of light guiding capillary 15 which has an unbeveled perpendicular front face. At the end 39 of light guiding capillary 15, radiation 17 exits and spreads in a cone-like shape and is collimated by a concave mirror 40 into a parallel beam. A focusing lens 41 focuses radiation 17 onto an end of a bundle of light guiding fibers 43 that directs radiation 17 for analysis to a spectrometer (not shown) as indicated by arrow 44. For Raman spectroscopy an optional edge of bandpass filter 42 can be inserted in the beam of radiation 17 to remove elastically scattered laser light.

EXAMPLES

Example 1

Methane Oxidation on Pt Coated α-Al₂O₃ Foam Catalyst from 1.4 Bar to 15 Bar

The reactor described above was used to study methane oxidation on autothermally operated Pt coated α-Al₂O₃ foam catalysts at pressures from 1.4 to 15 bar. The pressure was varied to investigate whether gas phase reactions proceed in parallel to catalytic reactions and whether transport limitations occur. The catalyst section was formed by two α-Al₂O₃ foam catalysts (45 pores per linear inch, Vesuvius Hi-Tech) coated by 0.6 wt % Pt and sandwiched between two uncoated 80 ppi foams which served as front heat shield and as back heat shield, respectively. In the further discussion, taking into account a flow from bottom to top, the front heat shield is denoted FHS, the two Pt coated catalyst foams are denoted Pt and Pt, and the back heat shield is denoted BHS. Channels having a diameter of 1 mm for accommodating sampling capillary 4 were drilled before coating the catalyst foams with Pt. A gas mixture consisting of $CH_4/O_2/Ar$ (911/228/858 ml·min⁻¹, respectively) was fed through reactor tube 18 from bottom to top. To assign a catalyst temperature to each gas species composition, the solid temperature was measured by means of a pyrometer fiber inserted in sampling capillary 4 and aligned with the side sampling orifice 6 to obtain an arrangement according to FIG. 1a.

Profiles were measured for pressures of 1.4 bar, 5.1 bar, 10 bar and 15 bar. All data are summarized in FIG. 4.

Although the experimental results shall not be discussed in detail, the profiles reveal immediately interesting details of the methane oxidation mechanism. It can be seen that there exists a short zone behind the catalyst entrance where $CH_4$ and $O_2$ are rapidly converted. The chemistry in this entrance zone which extends from 0-2400 μm can be described by Equation 1 with x taking values between $0 \leq x \leq 2$ and y taking values between $0 \leq y \leq 1$.

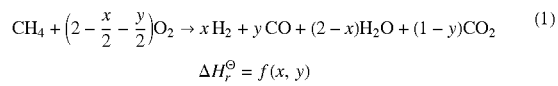

$$CH_4 + \left(2 - \frac{x}{2} - \frac{y}{2}\right)O_2 \rightarrow xH_2 + yCO + (2-x)H_2O + (1-y)CO_2 \quad (1)$$

$$\Delta H_r^\ominus = f(x, y)$$

Figure 4:
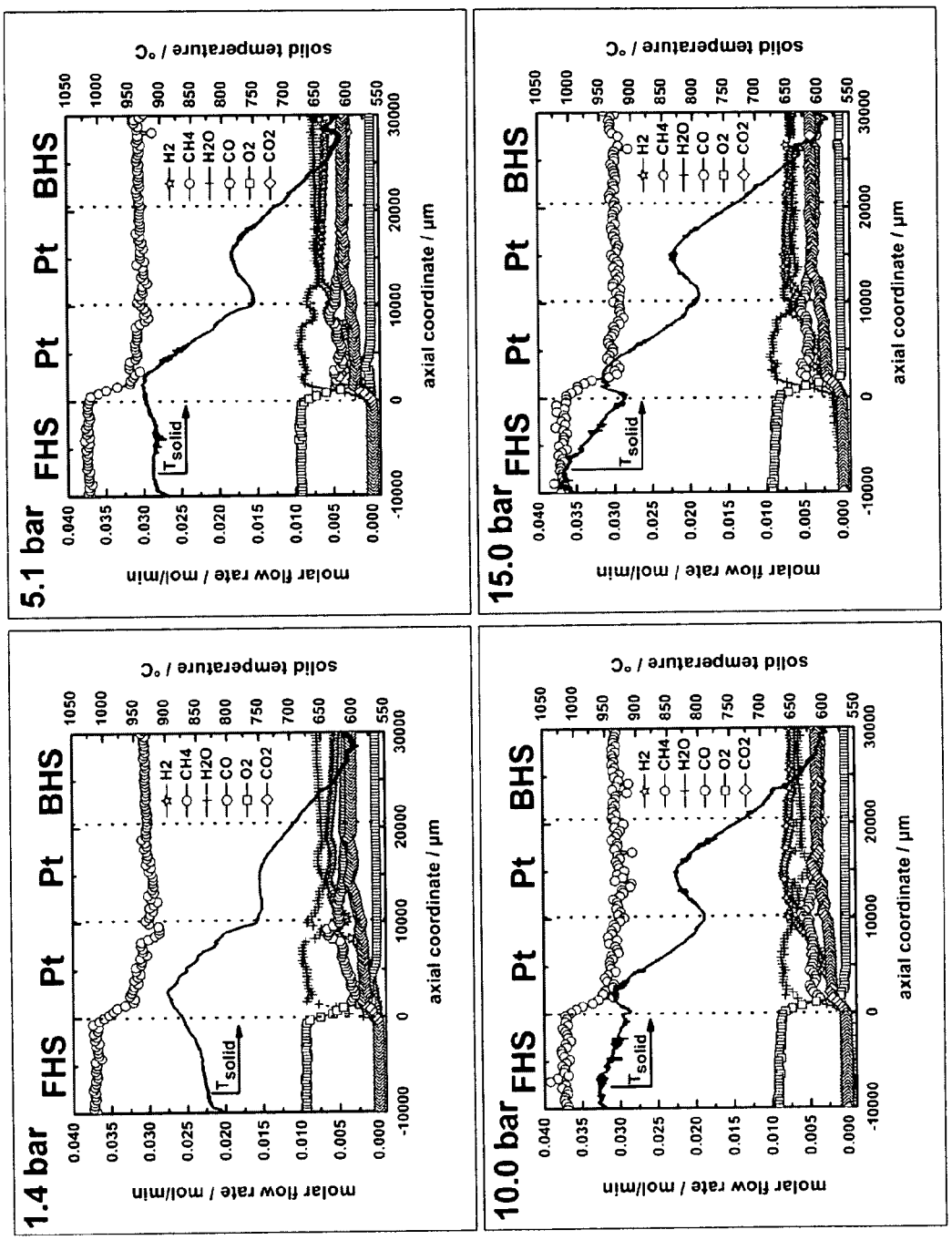
FIG. 4: diagrams of spatial profile measurements for methane oxidation on 0.6 wt % Pt coated 45 ppi $\alpha$-$Al_2O_3$ foam catalysts.

Non-catalytic methane total oxidation occurs for pressures p≥10 bar as can be seen from FIG. 4 (10 and 15 bar measurements) where a slight conversion of $O_2$ is already observed in the front heat shield accompanied by liberation of heat due to the high combustion enthalpy of methane ($CH_4 + 2O_2 \rightarrow CO_2 + 2H_2O$, $\Delta H_r^\ominus = -803$ kJ·mol⁻¹). This explains why at 10 and 15 bar the temperature in the front heat shield FHS is higher than in the catalyst section Pt and Pt.

Upon complete $O_2$ conversion, secondary reactions like steam reforming ($CH_4 + H_2O \rightarrow CO + 3H_2$) and watergas shift ($CO + H_2O \rightarrow CO_2 + H_2$) are taking place until the mixture leaves the catalyst (2400-20500 μm).

Figure 5:
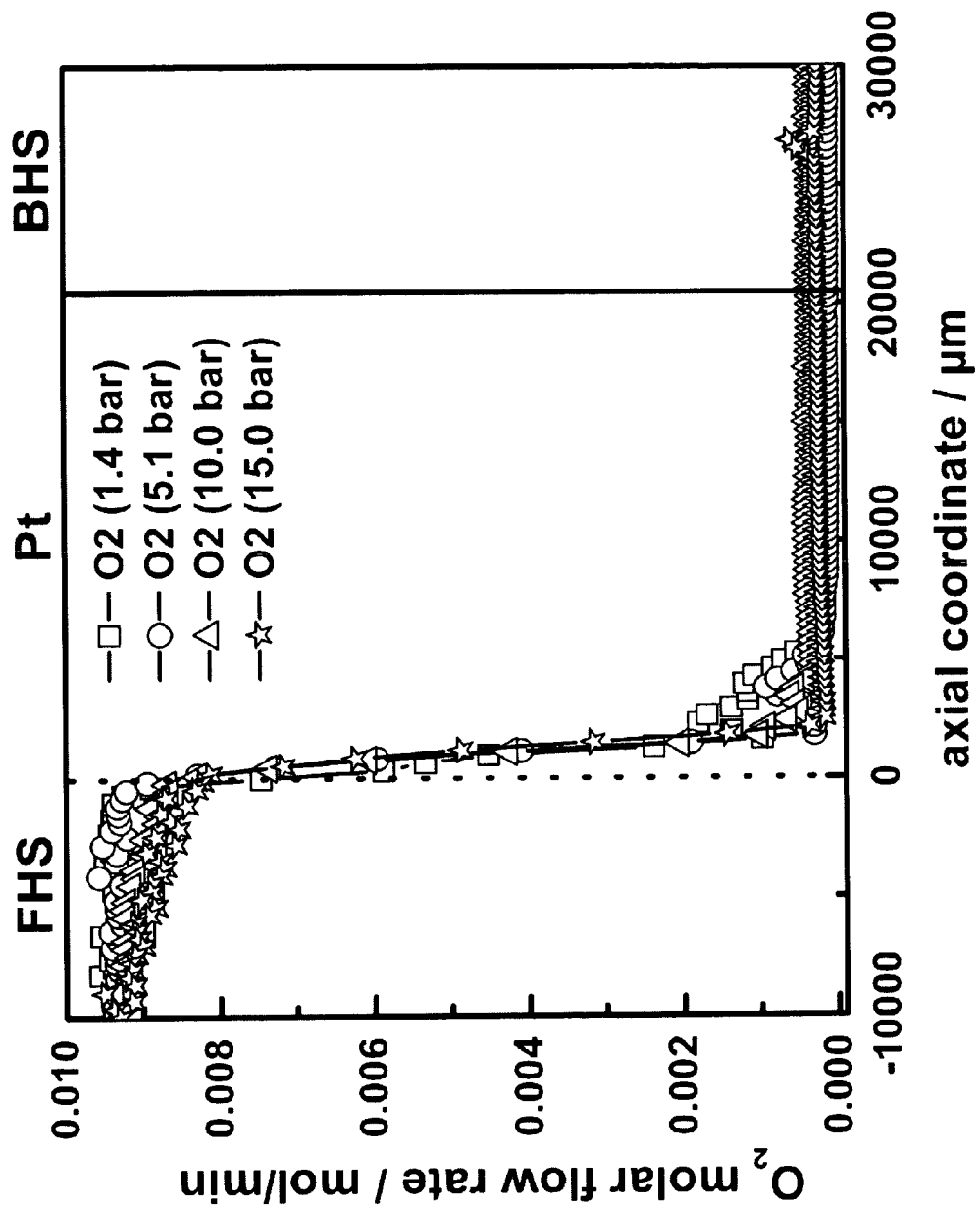
FIG. 5: oxygen profiles from FIG. 4 superimposed.

It is very interesting to note that the $O_2$ profiles fall on top of each other and are highly linear regardless whether the reactor pressure was 1.4, 5.1, 10 or 15 bar (FIG. 5). By formulating an $O_2$ mass balance it can be shown that this behavior corresponds to a zeroth order kinetics which can be chemically understood in terms of blocking of most of the active catalytic sites by one dominant surface species. Independent in situ Raman measurements on a Pt foil indicate that this species is probably carbon (data not shown).

Example 2

Methane Oxidative Coupling on Li/MgO Coated α-Al₂O₃ Foam Catalysts at Atmospheric Pressure In this example the oxidative coupling of methane to C2 hydrocarbons ($C_2H_6$, $C_2H_4$ and $C_2H_2$) on Li doped MgO is investigated. This reaction is debated in the literature in terms of a so-called heterogeneous-homogeneous mechanism which means that the Li/MgO catalyst produces $CH_3$· radicals which desorb into the gas phase and couple there to $CH_3$—$CH_3$ which is further dehydrogenated to $CH_2$=$CH_2$. The methane oxidative coupling, even though highly attractive from an industrial point of view, is still at the research stage as one-pass yields higher than about 25% cannot yet be achieved. The reason for this virtual bond is still unclear.

Figure 6:
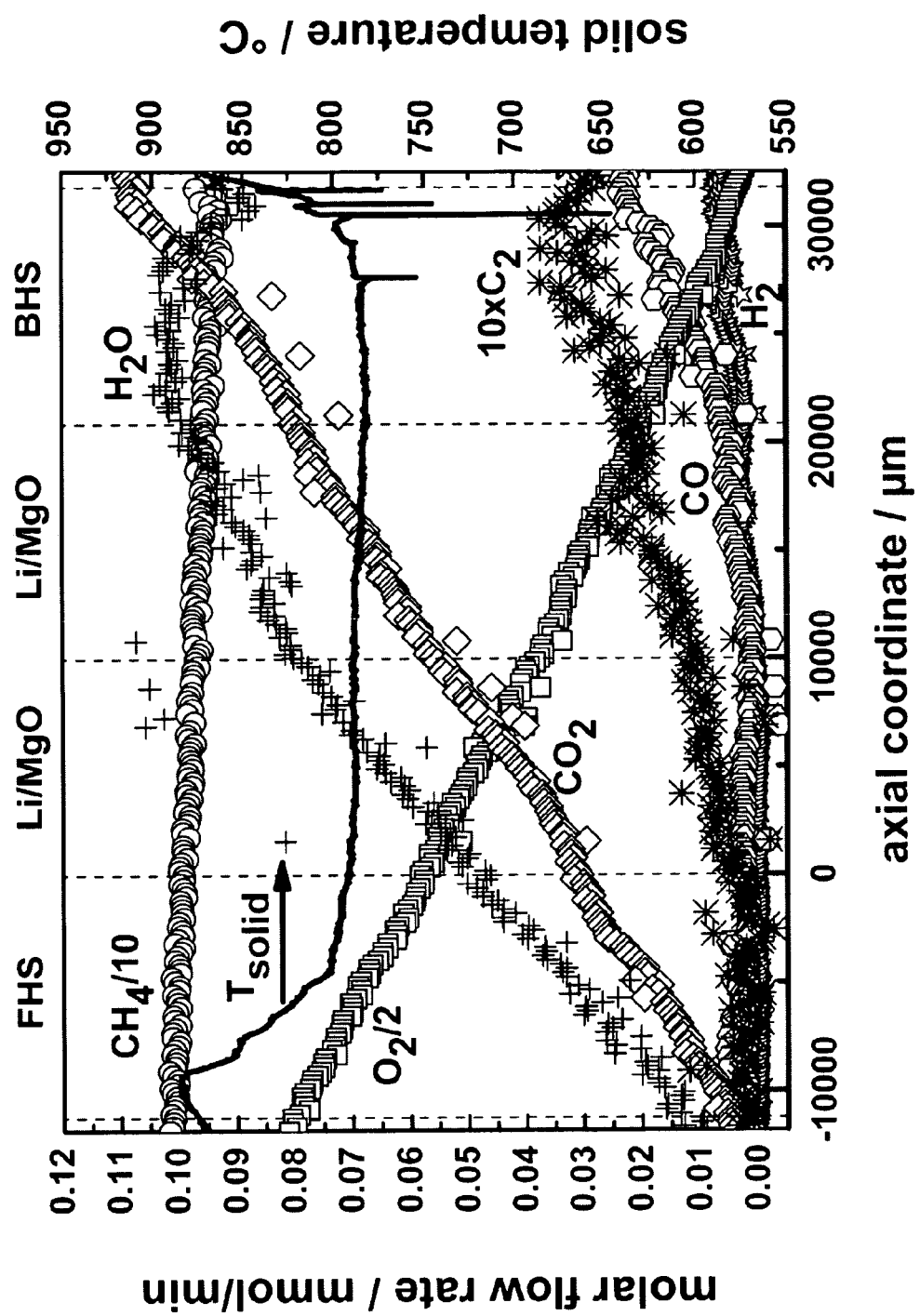
FIG. 6: spatial profile measurements for methane oxidative coupling on Li/MgO; Catalyst section formed by two 0.8 wt % Li/MgO coated $\alpha$-$Al_2O_3$ foams.

The experiment was conducted in an analogous manner as described in Example 1 with the only difference that two 0.8 wt % Li/MgO coated α-$Al_2O_3$ foams served as catalyst bed, much lower flow rates were used. ($CH_4/O_2/Ar$=25.6/6.4/8.0 ml·min$^{-1}$), and that the reactor was heated to about 780° C. Very low total flow rates had to be used as methane oxidation on Li/MgO is much slower than on Pt and external heating was necessary as the reaction does not produce sufficient heat for autothermal operation. The spatial profiles are depicted in FIG. 6. In FIG. 6, the inert packings are denoted in flow direction as front heat shield FHS and back heat shield BHS sandwiching the two Li/MgO coated catalyst foams denoted Li/MgO and Li/MgO. Again, a pyrometer fiber was used as temperature probe to measure the solid temperature.

The pyrometer temperature profile shows that the reactor is very isothermal in the catalytic section (788±2° C.), which is an important requirement for kinetic measurements. The increase of the temperature curve towards the ends of both heat shields is a measurement artifact, as thermal radiation from the much hotter heating coils of the split furnace 37 is reflected by upper and lower mounting clamps 19 and 20, respectively, into the heat shields. Longer heat shields would eliminate this problem.

The species profiles reveal a number of interesting details. It can be seen that methane is lost with constant rate by total oxidation to $CO_2$ and $H_2O$. This total oxidation occurs obviously in the gas phase as it is not restricted to the catalyst section. C2 coupling products (at 780° C. only $C_2H_6$+$C_2H_4$) are not formed before the reactants hit the catalyst section indicating that no pre-catalytic C2 formation occurs. Even though only small amounts of C2 are formed the profile shows clearly that C2 is formed with a constant rate and that the formation continues behind the catalyst section in the back heat shield. This could be due to loose catalyst material that has been transported by the gas flow to the back heat shield. However, as the gas flow is extremely slow and directed against gravity this explanation is not very likely. The post-catalytic C2 production is more likely an indication for gas phase formation of C2 products triggered by the catalyst in line with the postulated "heterogeneous-homogeneous mechanism." CO seems to be a secondary product as its formation starts quite late in the catalyst section. Virtually no hydrogen is formed at all.

Example 3

Figure 7:
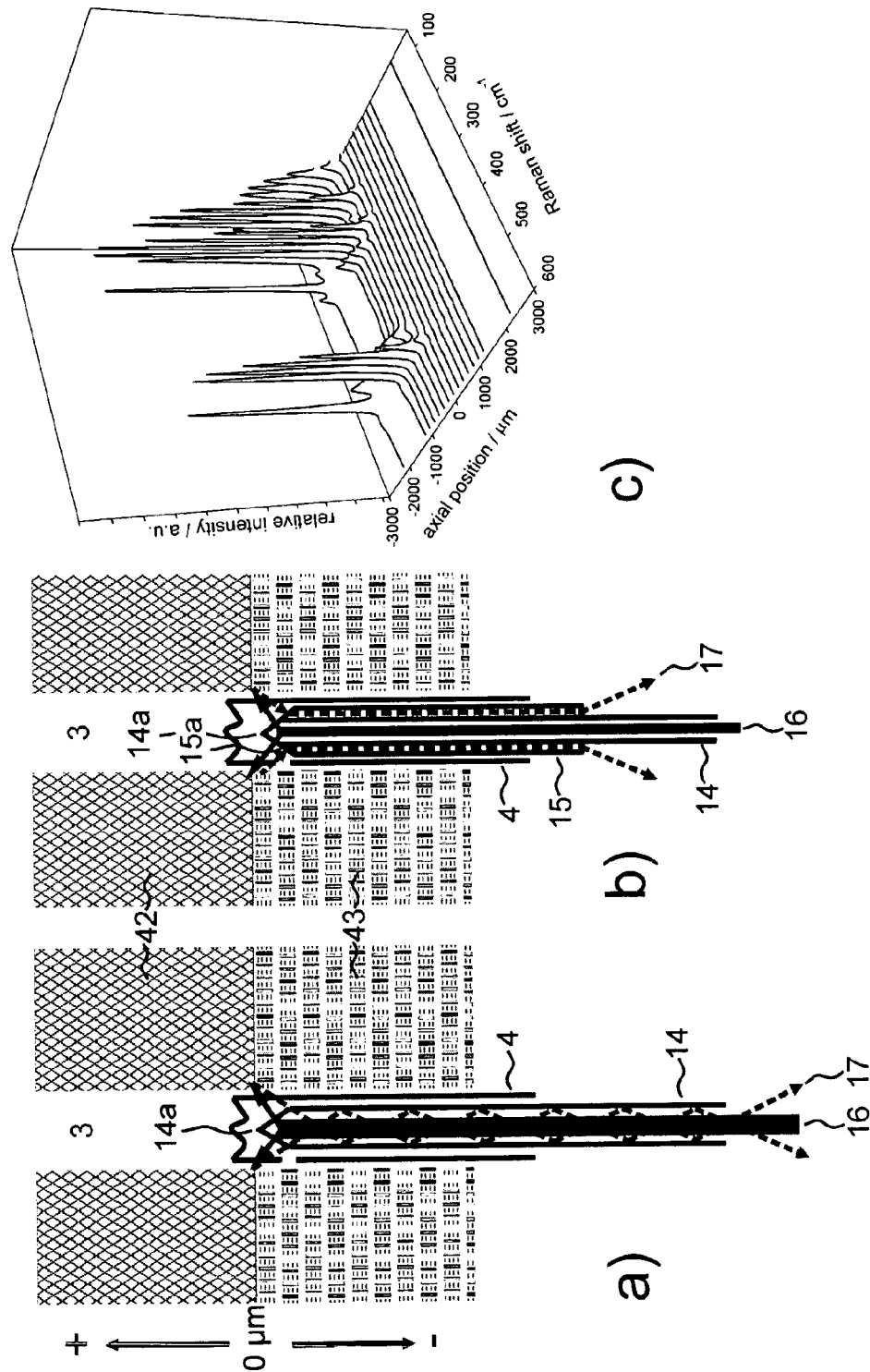
FIG. 7: a) an arrangement for demonstration of spatially resolved Raman spectroscopy on a cylindrical stack of graphite-sulfur cylinders using a single light guiding fiber A b) an arrangement for demonstration of spatially resolved Raman spectroscopy on a cylindrical stack of graphite-sulfur cylinders using a light guiding fiber inserted into a light guiding capillary B; c) spatially resolved Raman spectra measured around the graphite-sulfur transition obtained using a single light guiding fiber A.

Spatially Resolved Raman Spectroscopy in a Cylindrical Graphite/Sulfur Stack as a Model System To demonstrate that spatially resolved spectroscopy is possible, Raman spectroscopy was chosen as spectroscopic method. For demonstration of spatial resolution, an experiment as shown in FIG. 7 was set up. A stack of a graphite cylinder 42 and a sulfur cylinder 43 both with 15 mm outer diameter was prepared with a 1 mm central channel 3 so that a sharp transition from a very poor highly absorbing Raman scatterer (graphite) to an excellent Raman scatterer (sulfur) was created (FIGS. 7a and 7b). As shown in FIG. 7a, the axial position of the interface between graphite cylinder 42 and sulfur cylinder 43 was set to 0 µm. Positions in the graphite cylinder were chosen to have a positive sign, those in the sulfur cylinder to have a negative sign. Both, optical sensor A comprising a single light guiding fiber 14 beveled at the fiber tip 14a and optical sensor B comprising a light guiding fiber 14 beveled at the fiber tip 14a inside a light guiding capillary 15 beveled at its front surface 15a as described in FIGS. 1b), 1c) and 3) were tested. In one set of experiments each sensor was inserted in the sampling capillary 4 and in a second experiment each sensor projected from the tip of sampling capillary 4. Light 16 (300 mW, 488 nm) from an Argon ion laser was coupled into both sensors. Sensor A comprised a bare fluorine doped fused silica fiber 14 (OD=440 µm, Optronis GmbH). The fiber comprised a cone-shaped beveled tip 14a, so that the acceptance angle of fiber 14 was almost perpendicular to the longitudinal, fiber axis. Scattered light was collected by the same fiber 14 and transferred into a fiber bundle 43 (CeramOptec GmbH) consisting of 19 fluorine doped fused silica fibers (OD=110 µm) arranged in a circular closed package at the reactor side and on top of each other in form of a line (height 2 mm) at the spectrometer side.

Sensor B (FIG. 7b) comprised a light guiding single fluorine doped fused silica fiber 14 (OD=120 µm, Optronis GmbH) inserted into a light guiding fluorine doped fused silica capillary 15 (ID=150 µm, Optronis GmbH). The light guiding fluorine doped fused silica capillary 15 was chosen to be shorter than light guiding fused silica fiber 14. At the end of sensor B that was located in the graphite/sulfur stack, the tip 14a of fiber 14 and the front surface 15a of capillary 15 were aligned and beveled as a cone as shown in the inset in FIG. 3 to emit and collect light nearly perpendicular to the longitudinal axis of sensor B. At the other end, fiber 14 and capillary 15 were spatially separated as shown in FIG. 3. The end of capillary 15 was at position 39. Light 17 was collected by the arrangement shown in FIG. 3 and focused into a fiber bundle 43 (CeramOptec GmbH) consisting of 19 fluorine doped fused silica fibers (OD=110 µm) arranged in a circular closed package at the reactor side and on top of each other in form of a line (height 2 mm) at the spectrometer side.

In all experiments the scattered light was analyzed by means of a triple filter Raman spectrometer (TriVista S&I GmbH) operated in subtractive mode.

Figure 8:
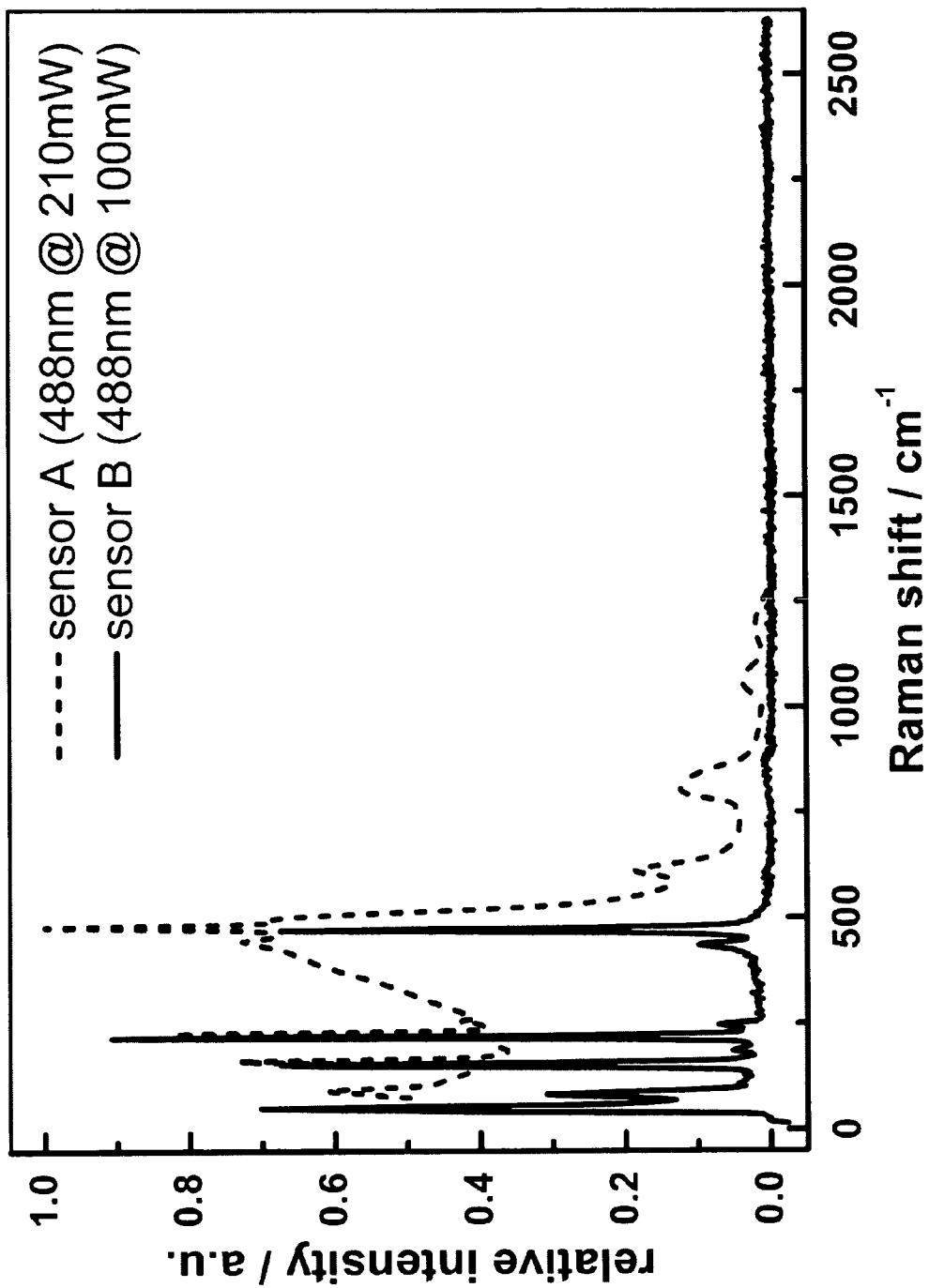
FIG. 8: comparison of the relative contribution of Raman scattering from the sample (sulfur) and the sensor material (quartz) by means of a sulfur spectrum measured with an optical sensor having a single light guiding fiber A and with an optical sensor having a light guiding fiber inserted into a light guiding capillary B.

For both optical sensors A and B, the actual measured spectra are a linear superposition of the Raman spectrum of the sensor material (fused silica) and the Raman spectrum of the sample at the place of analysis. The contribution of the signal from the sensor material cannot be fully eliminated experimentally in the spatially resolved Raman measurements demonstrated here, as no optical filters can be used at the tip of either sensor A or B due to the small dimensions of the sensors and the high temperatures in the quartz reactor tube 18. Nevertheless, as shown in FIG. 8, sensor B nearly eliminates the Raman background of the sensor material due to spatial decoupling of excitation light 16 and interacted light 17. In any case, the Raman background of the fiber material is constant and can be subtracted after normalization so that only the spectrum of the sample remains. If the sample is a good Raman scatterer, already the simple Sensor A gives excellent results as shown in FIG. 7c) for the graphite/sulfur experiment. If weak scatterers have to be measured, Sensor B gives superior results as will be shown later.

Figure 9:
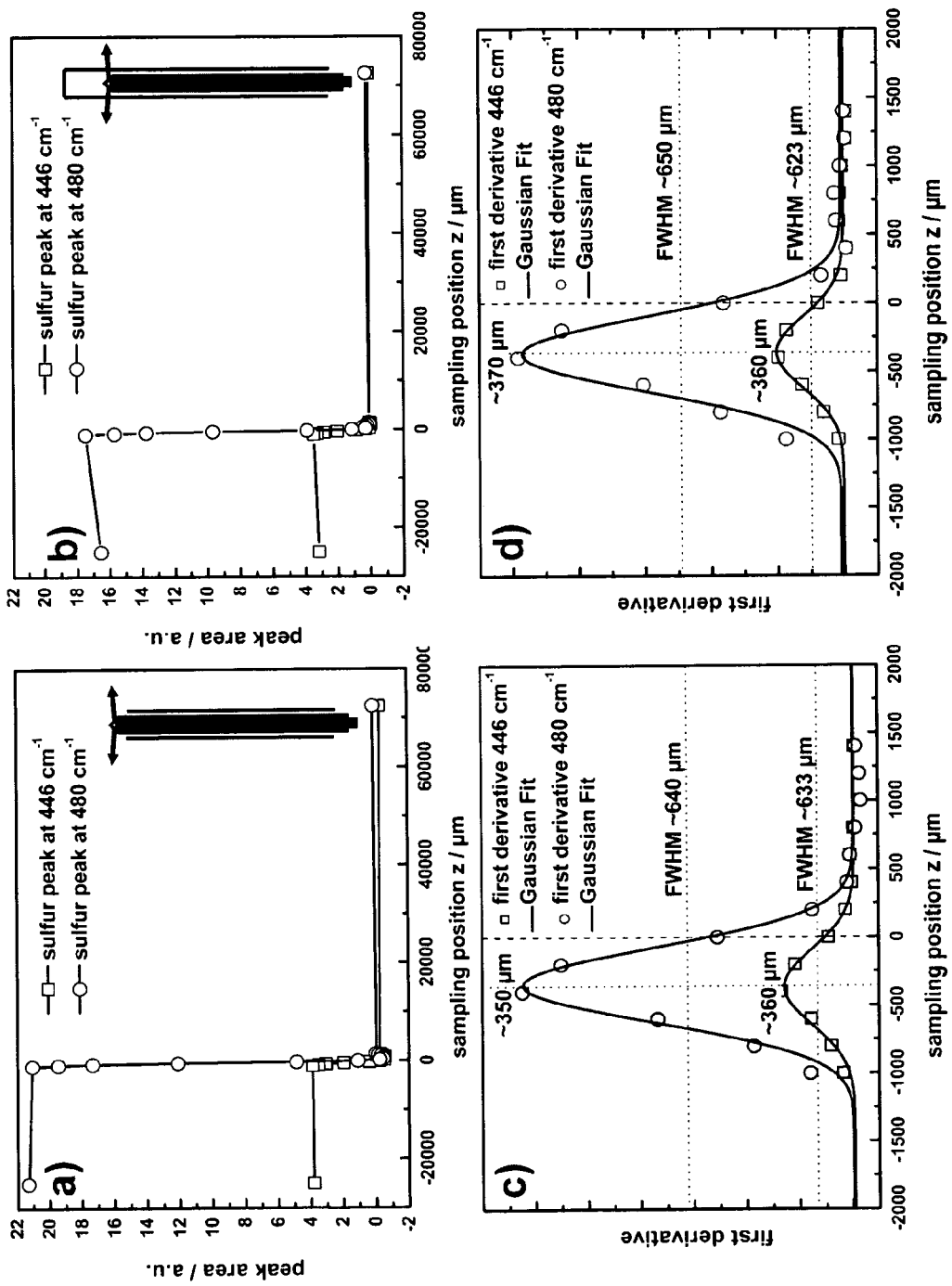
FIG. 9: determination of position accuracy and spatial resolution of spatially resolved Raman measurements using an optical sensor having a single light guiding fiber A. Upper Panels: peak areas of sulfur Raman peaks at 446 $cm^{-1}$ and 480 cm$^{-1}$ plotted against sensor position with the fiber tip outside the sampling capillary (FIG. 9a) and inside of the sampling capillary (FIG. 9b). Lower panels: first derivatives (points) fitted by a Gaussian function (solid line) for the tip outside the sampling capillary (FIG. 9c) and inside the sampling capillary (FIG. 9d)

The position accuracy and the spatial resolution of the method was determined for Sensor A and B and evaluated as shown exemplarily for Sensor A in FIG. 9. One intense sulfur Raman peak at 480 cm$^{-1}$ and one weak sulfur Raman peak at 446 cm$^{-1}$ [1] were integrated and plotted against position (FIGS. 9a) and b)). This was done both for the data measured when the Sensor tip was outside of the sampling capillary (FIG. 9a)) and when the sensor tip was inside the sampling capillary (FIG. 9b). The step like functions obtained (FIGS. 9a) and b)) are a convolution between a nearly perfect step function (sulfur-graphite interface) and the spread function of the optical arrangement (fiber+spectrometer). The latter can be obtained by calculating the first derivative of the spatial data around the sulfur-graphite transition (FIGS. 9c) and 9d)). The analysis shows that the position accuracy is excellent as only a small offset of about 350-370 µm exists. This small offset is probably due to the fact that the acceptance angle of the fiber is somewhat less than 90° and can be accounted for if necessary. The spread function of the optical system can be well fitted by a Gaussian function (solid lines in the lower panels of FIG. 9). If the Full Width at Half Maximum (FWHM) of the Gaussian is taken as a measure for the spatial resolution of the method, then a spatial resolution of 620-650 µm can be achieved which will be more than sufficient for catalysis applications taking into account that catalytic variations occur over many millimeters if not centimeters.

Finally, it will be demonstrated that it is possible to measure also Raman spectra of catalytically relevant materials forming catalyst bed 1 which are typically much weaker Raman scatterers than sulfur which was only chosen for demonstration purposes of spatially resolved Raman measurements. 30% by weight Molybdenumtrioxide, $MoO_3$, a catalyst active for oxidative dehydrogenation of ethane to ethylene was supported on 1 mm $\gamma$-$Al_2O_3$ spheres and filled in the quartz reactor tube 18 shown in FIG. 2 to form catalyst bed 1. Sensor B was inserted in the sampling capillary 4 and its tip was positioned in the center of the supported $MoO_3$ catalyst bed 1. Laser light 16 of 532 nm wavelength and 1 W power was coupled into Sensor B according to FIG. 3 and the scattered light 17 was collected and integrated for 15 min again as described in FIG. 3. As visible by comparison of the dotted line in FIG. 10a) showing the Raman spectrum of the blank Sensor B with the solid line showing the Raman spectrum of Sensor B positioned in the supported $MoO_3$ catalyst bed 1, the solid line is a linear superposition of signal originating from the fiber material and the $MoO_3$ catalyst 1. After subtraction of the fiber spectrum, the characteristic Raman spectrum of $MoO_3$ is obtained as shown in FIG. 10b.

In summary it could be demonstrated that spatially resolved optical spectroscopy is possible with the invention described herein.

REFERENCE NUMERALS

1 catalyst bed
2 inert packing
3 channel in catalyst bed/inert packings
4 sampling capillary
5 closed end of sampling capillary
6 sampling orifice
7 position of temperature and optical sensor
8 closed end of sampling capillary
9 rotation of sampling capillary
10 up and down movement of sampling capillary
11 gap in sampling capillary for fluid sampling
12 fluid flow into reactor
13 fluid flow out of reactor
14 light guiding fiber for optical spectroscopy (part of optical sensor A and B)
14a beveled tip of light guiding fiber 14
15 light guiding capillary (part of optical sensor B)
15a beveled front surface of light guiding capillary 15
16 light for excitation
17 light emitted, absorbed, reflected or scattered by the sample
18 quartz reactor tube
19 upper mounting clamp
20 lower mounting clamp
21 stainless steel flange
22 base plate
23 movable cover plate
24 linear bearings
25 frame
26 microvolume cross
27 rotary stage
28 linear stage
29 mass flow controllers
30 tube in tube heat exchanger/condenser
31 reservoir for condensable species
32 pressure controllers
33 pressure gauge
34 burst disk
35 pyrometer
36 motor control units
37 split furnace
38 microvolume cross holder
39 end of light guiding capillary in sensor B
40 concave mirror
41 focussing lens
42 optional edge or bandpass filter
43 fiber bundle
44 light for spectral processing

The invention claimed is:
1. A system for in-situ spectroscopic measurements in heterogeneous catalytic reactors comprising:
   a reactor comprising a reactor chamber,
   an optical radiation source,
   a device for collecting optical radiation scattered by a sample inside the reactor chamber, wherein the device comprises a radiation guide for transmitting the optical radiation from the optical radiation source to the sample and transmitting the optical radiation to a device for processing and displaying spectroscopic information arranged outside the reactor, and the radiation guide further comprises a tip situated in the reactor chamber, and
   a sampling capillary having an orifice situated inside the reactor chamber for collecting a fluid sample inside the reactor chamber and an end situated outside the reactor chamber connected to an analytical device for at least one of quantitative and qualitative analysis
   wherein the tip of the radiation guide is arranged within the sampling capillary proximal to the orifice and is configured to receive the scattered optical radiation.
2. The system according to claim 1, characterized in that the device for collecting optical radiation comprises a first radiation guide for collecting radiation scattered by a sample and a second radiation guide for guiding radiation onto the sample for excitation.
3. The system according to claim 2 characterized in that at least one of said first and second radiation guides has the form of a fiber.
4. The system according to claim 2 characterized in that the first radiation guide for collecting radiation scattered by the sample has the form of a light guiding capillary and the second radiation guide for guiding radiation onto the sample for excitation has the form of a fiber positioned within the light guiding capillary.
5. The system according to claim 1, characterized in that the tip of the radiation guide for collecting optical radiation in the reaction chamber comprises a beveled tip.

6. The system according to claim 1, characterized in that the radiation guide is movable inside the reactor.

7. The system according to claim 1, characterized in that the device for collecting optical radiation is combined with a temperature-sensitive sensor.

8. The system according to claim 7, characterized in that the temperature-sensitive sensor is arranged proximal to the orifice.

9. Method for analyzing a reactor state comprising the steps:
providing a system for in-situ spectroscopic measurements in heterogeneous catalytic reactors according to claim 1;
collecting the fluid sample inside the reactor chamber of said system through the orifice of the sampling capillary of said system and analyzing the fluid sample with the analytical device connected to the sampling capillary;
irradiating the sample inside the reactor chamber of said system with the optical radiation from the optical radiation source,
collecting scattered optical radiation from the sample inside the reactor chamber through a tip of a radiation guide within the sampling capillary, wherein the tip is proximal to the orifice; and
processing and displaying spectroscopic data obtained from the scattered optical radiation collected by the radiation guide by the device for processing and displaying spectroscopic information located outside the reaction chamber, thus providing information on the reactor state.

10. Method according to claim 9, wherein spectroscopic information is collected at a first position inside the reactor chamber to obtain a first spectrum and spectroscopic information is collected at a second position inside the reactor chamber to obtain a second spectrum.

11. Method according to claim 9, wherein the composition of the sample is analyzed.

12. Method according to claim 9, wherein a temperature is determined inside the reactor chamber.

13. A system for in-situ spectroscopic measurements in heterogeneous catalytic reactors comprising:
a reactor comprising a reactor chamber,
a device for collecting optical radiation emitted by a sample inside the reactor chamber, wherein the device comprises a radiation guide for transmitting the optical radiation to a device for processing and displaying spectroscopic information arranged outside the reactor, and the radiation guide further comprises a tip situated in the reactor chamber configured to receive the optical radiation, and
a sampling capillary having an orifice situated inside the reactor chamber for collecting a fluid sample inside the reactor chamber and an end situated outside the reactor chamber connected to an analytical device for at least one of quantitative and qualitative analysis
wherein the radiation guide is configured such that the optical radiation is capable of entering and exiting the tip, and the tip is arranged within the sampling capillary proximal to the orifice.

14. A system for in-situ spectroscopic measurements in heterogeneous catalytic reactors comprising:
a reactor comprising a reactor chamber,
an optical radiation source,
a device for collecting reflected optical radiation from a sample inside the reactor chamber, wherein the device comprises a radiation guide for transmitting the optical radiation from the optical radiation source to the sample and transmitting the reflected optical radiation from the sample to a device for processing and displaying spectroscopic information arranged outside the reactor, and the radiation guide further comprises a tip situated in the reactor chamber configured to receive the reflected optical radiation,
a sampling capillary having an orifice situated inside the reactor chamber for collecting a fluid sample inside the reactor chamber and an end situated outside the reactor chamber connected to an analytical device for at least one of quantitative and qualitative analysis, and
wherein the radiation guide is configured such that the optical radiation is capable of entering and exiting the tip, and the tip is arranged within the sampling capillary proximal to the orifice.

* * * * *